(12) United States Patent
Wang

(10) Patent No.: US 11,073,524 B2
(45) Date of Patent: Jul. 27, 2021

(54) DEVICE FOR DETECTION OF VITAMIN D METABOLITES

(71) Applicant: Affimedix, Inc., Santa Clara, CA (US)

(72) Inventor: Kevin C. Wang, San Francisco, CA (US)

(73) Assignee: Affimedix, Inc., Hayward, CA (US)

( * ) Notice: Subject to any disclaimer, the term of this patent is extended or adjusted under 35 U.S.C. 154(b) by 266 days.

(21) Appl. No.: 16/041,582

(22) Filed: Jul. 20, 2018

(65) Prior Publication Data

US 2019/0086430 A1  Mar. 21, 2019

Related U.S. Application Data

(63) Continuation of application No. PCT/US2017/014620, filed on Jan. 23, 2017.

(60) Provisional application No. 62/286,297, filed on Jan. 22, 2016.

(51) Int. Cl.
| | | |
|---|---|---|
| *G01N 33/82* | (2006.01) | |
| *G01N 33/543* | (2006.01) | |
| *G01N 33/558* | (2006.01) | |
| *C07K 16/44* | (2006.01) | |

(52) U.S. Cl.
CPC ............. *G01N 33/82* (2013.01); *C07K 16/44* (2013.01); *G01N 33/543* (2013.01); *G01N 33/54306* (2013.01); *G01N 33/558* (2013.01); *C07K 2317/32* (2013.01)

(58) Field of Classification Search
CPC ........... G01N 33/558; G01N 33/54386; C07K 2317/32
See application file for complete search history.

(56) References Cited

U.S. PATENT DOCUMENTS

| | | | | |
|---|---|---|---|---|
| 7,393,696 B2 * | 7/2008 | Roth | ..................... | A61D 17/006 435/287.1 |
| 7,482,162 B2 | 1/2009 | Laurie et al. | | |
| 7,749,712 B2 * | 7/2010 | Pulli | ..................... | G01N 33/542 435/7.1 |
| 9,599,608 B2 * | 3/2017 | Omi | ..................... | G01N 33/531 |
| 2013/0059825 A1 | 3/2013 | Sahakian et al. | | |
| 2014/0162294 A1 | 6/2014 | Yuan et al. | | |
| 2014/0370616 A1 | 12/2014 | Gupta et al. | | |
| 2015/0037813 A1 | 2/2015 | Omi et al. | | |
| 2015/0118689 A1 | 4/2015 | Egan et al. | | |
| 2015/0293085 A1 | 10/2015 | Anderberg et al. | | |

FOREIGN PATENT DOCUMENTS

| | | |
|---|---|---|
| CN | 104062440 A | 9/2014 |
| JP | 2008533472 A | 8/2008 |
| WO | WO-03014726 A1 | 2/2003 |
| WO | WO-2004063704 A2 | 7/2004 |
| WO | WO-2006099191 A2 | 9/2006 |
| WO | WO-2007039194 A1 | 4/2007 |
| WO | WO-2008039266 A2 | 4/2008 |
| WO | WO-2009069017 A1 | 6/2009 |
| WO | WO-2012162165 A2 | 11/2012 |
| WO | WO-2014113770 A1 | 7/2014 |
| WO | WO-2014114780 A1 | 7/2014 |
| WO | WO-2014196803 A1 | 12/2014 |
| WO | WO-2016091755 A1 | 6/2016 |
| WO | WO-2017127833 A1 | 7/2017 |

OTHER PUBLICATIONS

Goel et al. "Plasticity within the Antigen Combining Site May Manifest as Molecular Mimicry in the Humoral Immune Response", The Journal of Immunology 173(12)7358-7367, 2004.*
Edwards et al. "The remarkable flexibility of the human antibody repertoire; isolation of over one thousand different antibodies to a single protein, BLyS" J. Mol. Biol. (2003) 334, 103-118, DOI: 10.1016/j.jmb.2003.09.054.*
Lloyd et al. "Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168, https://doi.org/10.1093/protein/gzn058.*
Brown et al. "Tolerance of single, but not multiple, amino acid replacements in antibody VH CDR 2: a means of minimizing B cell wastage from somatic hypermutation?", J Immunol. May 1996; 156(9):3285-91.*
Vajdos et al. "Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4.*
Harlow, E. and Lane, D., Antibodies: A Laboratory Manual (1988) Cold Spring Harbor Laboratory Press, Cold Spring Harbor, NY, pp. 23-26.*
Lederman et al. "A single amino acid substitution in a common African allele of the CD4 molecule ablates binding of the monoclonal antibody, OKT4" Mol Immunol. Nov. 1991; 28(11):1171-81.*
Colman et al. Research in Immunology, 1994; 145(1): 33-36.*
Janeway et al. Immunobiology: the Immune System in Health and Disease (1999), Elsevier Science Ltd/Garland Publishing, New York, NY, Fourth Edition, pp. 86-88.*
Almagro et al. "Humanization of Antibodies", Frontiers in Bioscience 13, 1619-1633, 2008.*
Arneson, et al. Current Methods for Routine Clinical Laboratory Testing of Vitamin D Levels. Laboratory Medicine. vol. 44. Issue 1. Feb. 2013. pp. e38-e42. DOI: 10.1309/LMONQZQ27TIN7XFS.
EP17742126.0 Extended European Search Report dated Jul. 5, 2019, (9 pages total).

(Continued)

*Primary Examiner* — Christine Foster
(74) *Attorney, Agent, or Firm* — Wilson Sonsini Goodrich & Rosati

(57) ABSTRACT

The present invention provides methods, devices, and compositions to rapidly detect analytes, including small analytes, using a lateral flow device. Described herein is such a lateral flow device that can detect and quantify vitamin D in a whole blood, serum, or plasma sample by employing a sandwich-based immunoassay.

23 Claims, 10 Drawing Sheets

Specification includes a Sequence Listing.

(56) References Cited

OTHER PUBLICATIONS

Li, et al. High sensitivity immunoassays for small molecule compounds detection—Novel noncompetitive immunoassay designs. TrAC Trends in Analytical Chemistry. vol. 103. Jun. 2018. pp. 198-208. DOI: 10.1016/j.trac.2018.04.008.
Omi, et al. Noncompetitive immunoassay detection system for haptens on the basis of antimetatype antibodies. Clin Chem. Apr. 2015;61(4):627-635. doi: 10.1373/clinchem.2014.232728. Epub Feb. 18, 2015.
Voss, et al. Anti-metatype antibodies in immunoassays. Microchimica Acta. Sep. 1997. vol. 126. Issue 3-4. pp. 193-202. DOI: 10.1007/BF01242320.
International search report with written opinion dated Apr. 14, 2017 for PCT/US17/14620.
Lee, et al. A smartphone platform for the quantification of vitamin D levels. Lab Chip. Apr. 21, 2014;14(8):1437-42. doi: 10.1039/c3lc51375k.
Valcour, et al. A novel, fully-automated, chemiluminescent assay for the detection of 1,25-dihydroxyvitamin D in biological samples. J Steroid Biochem Mol Biol. Nov. 2016;164:120-126. doi: 10.1016/j.jsbmb.2015.08.005. Epub Aug. 21, 2015.
Jayaram, et al. Germline VH/VL pairing in antibodies. Protein Eng Des Sel. Oct. 2012;25(10):523-9. Epub Jul. 15, 2012.
Kohler, et al. Continuous cultures of fused cells secreting antibody of predefined specificity. Nature. Aug. 7, 1975;256(5517):495-7.

* cited by examiner

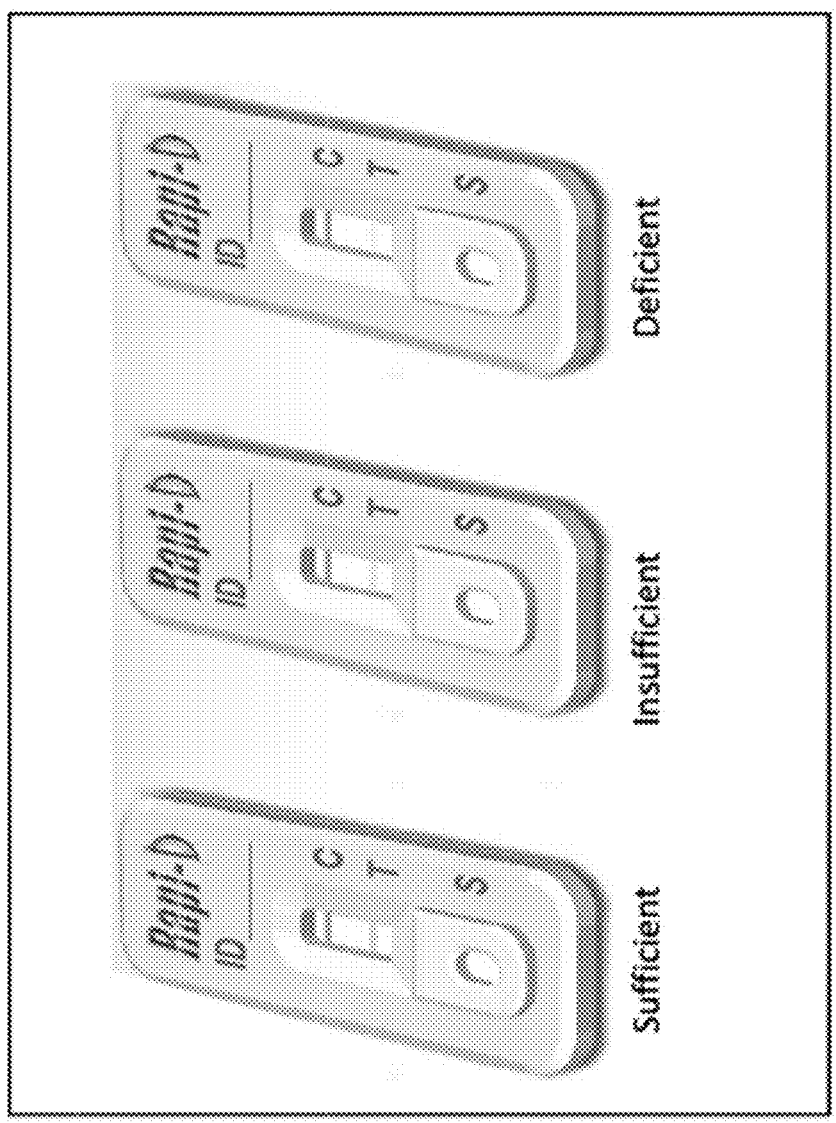
Fig. 1A
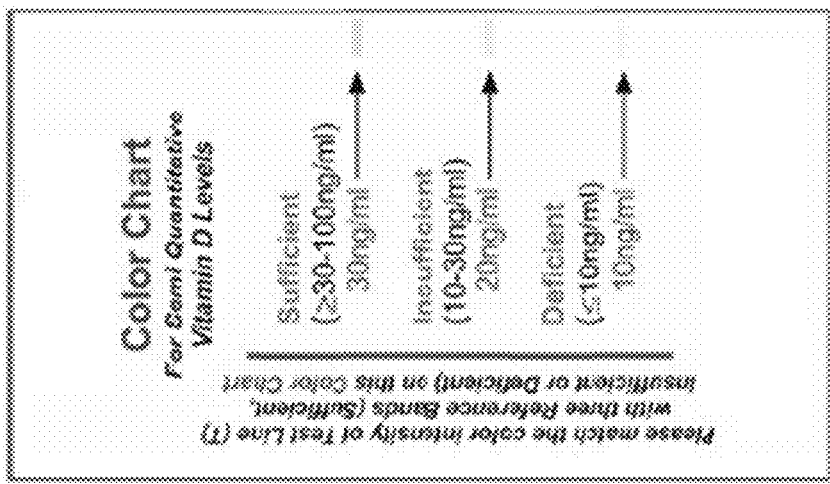
Fig. 1B
Fig. 1

DEVICE FOR DETECTION OF VITAMIN D METABOLITES

CROSS-REFERENCE

This application is a continuation application of International Patent Application No. PCT/US2017/014620, filed Jan. 23, 2017, which claims the benefit of U.S. Provisional Application No. 62/286,297, filed Jan. 22, 2016, each of which is incorporated by reference in its entirety.

SEQUENCE LISTING

The instant application contains a Sequence Listing which has been submitted electronically in ASCII format and is hereby incorporated by reference in its entirety. Said ASCII copy is named 49821-701.301.txt and is 22,877 bytes in size.

BACKGROUND OF THE INVENTION

Vitamin D refers to group of steroid hormones responsible for enhancing intestinal absorption of calcium and the regulation of its homeostasis. Two common forms of vitamin D are vitamin $D_2$ and vitamin $D_3$. Vitamin $D_3$ is naturally produced in the human skin through the exposure to ultraviolet light, whereas Vitamin $D_2$ is mainly obtained from foods and supplements. Vitamin $D_2$ and vitamin $D_3$ are biologically inactive; activation requires the transport of vitamin $D_2$ and vitamin $D_3$ to the liver where they can be metabolized by hydroxylation to an active form, referred to herein as 25-hydroxy vitamin D ("25-(OH)D"). Vitamin D binding protein DBP is the predominant serum transport protein for all vitamin D metabolites. DBP transports 95-99% of the total 25-OHD with only 1-5% carried by albumin and lipoproteins. Vitamin D deficiency has been linked to many diseases including osteoporosis, osteopenia, rickets, cancers, autoimmune diseases, cardiovascular diseases, and infectious diseases, and it is also associated with increased risk of mortality.

Unfortunately, vitamin D deficiency is a significant worldwide health concern and has become a global epidemic. An estimated 1 billion people globally do not have adequate vitamin D levels. Furthermore, it is estimated that 64% of Americans do not have enough vitamin D suboptimal vitamin D levels. The major cause of vitamin D deficiency is the lack of moderate sun exposure, which is the major source of vitamin D for most humans.

A 25-(OH)D blood test can be used to determine the circulating vitamin D concentration in a subject. The blood concentration of 25-(OH)D, including 25-OH($D_2$) and 25-OH($D_3$), is considered the best indicator of vitamin D status. The past decade has seen a world-wide increase in demand for the analysis of 25-(OH)D levels in patient populations.

Vitamin D is a challenging analyte to measure accurately, due to its highly lipophilic nature and high-affinity binding to vitamin D binding protein DBP. Current measurements are largely performed in specialist laboratories employing time-consuming methods, such as liquid chromatography-tandem mass spectrometry (LC-MS/MS) assay, radioimmunoassay (RIAs), enzyme-linked competitive immunosorbent assays (ELISAs), and competitive protein-binding assays (CPBA).

There exists a need for improved methods to detect and quantify vitamin D metabolites. Provided herein are methods, compositions, and devices to detect and quantify vitamin D metabolites by a simplified, rapid and accurate assay.

SUMMARY OF THE INVENTION

There exists a considerable need for alternative devices, methods, and kits for detecting and measuring one or more vitamin D molecules. The present invention addresses this need and provides additional advantages. In one aspect, the present invention provides for a test device for detecting one or more vitamin D molecules comprising: (a) a housing, contained therein: (i) a sample application pad configured to absorb a biological sample and transport the biological sample to a conjugate pad; (ii) the conjugate pad comprising a vitamin D binding agent that specifically binds to one or more vitamin D molecules; and (iii) a detection zone comprising a first region immobilized therein a detection antibody that specifically binds an epitope that is generated by complexing the vitamin D binding agent with the one or more vitamin D molecules.

In some embodiments provided herein, the one or more vitamin D molecules are selected from the group consisting of 25-hydroxyvitamin $D_2$, 25-hydroxyvitamin $D_3$, 25-hydroxyvitamin $D_4$, 25-hydroxyvitamin $D_5$, and 1,25-hydroxyvitamin $D_3$. In some embodiments provided herein, the one or more vitamin D molecules are selected from the group consisting of 25-hydroxyvitamin $D_2$ and 25-hydroxyvitamin $D_3$. In some embodiments provided herein, the one or more vitamin D molecules are 25-hydroxyvitamin $D_2$ and 25-hydroxyvitamin $D_3$. In some embodiments provided herein, the one or more vitamin D molecules consist of 25-hydroxyvitamin $D_2$. In some embodiments provided herein, the one or more vitamin D molecules consist of 25-hydroxyvitamin $D_3$.

In some embodiments provided herein, the detection zone further comprises a second region immobilized therein a third antibody that is capable of binding to the vitamin D binding agent whether or not the vitamin D binding agent is bound to the one or more vitamin D molecules. In some embodiments provided herein, the vitamin D binding agent is conjugated to a detection reagent. In some embodiments provided herein, the detection reagent is selected from the group consisting of gold particle, latex particle, carbon nanoparticle, selenium nanoparticle, silver nanoparticle, quantum dot, fluorescent compound, dye, enzyme and liposome. In some embodiments provided herein, the detection reagent is the gold particle. In some embodiments provided herein, the detection reagent is the latex particle.

In some embodiments provided herein, the sample application pad, the conjugate pad, and the detection zone are aligned from upstream to downstream along a fluid path through which the biological sample travels. In some embodiments provided herein, the test device further comprises a filtering component between the sample application pad and the conjugate pad configured to separate particulate portion of the biological sample from aqueous portion of the biological sample.

In one aspect, the present invention provides a method, comprising: applying a biological sample to the sample application pad of any one of the test devices disclosed herein; applying a chase buffer to the sample application pad; and detecting the one or more vitamin D molecules. In some embodiments provided herein, the method further comprises quantifying the one or more vitamin D molecules in the sample. In some embodiments provided herein, the quantifying classifies the blood sample as having a sufficient, an insufficient, or a deficient level of the one or more vitamin D molecules. In some embodiments provided herein, the sufficient level is at least 30 ng/mL. In some embodiments provided herein, the insufficient level is at least 10 ng/mL and less than 30 ng/mL. In some embodiments provided herein, the deficient level is less than 10 ng/mL. In some embodiments provided herein, the quantifying further comprises using an imaging device to provide an image of the detection membrane and software on a programmed computer configured to quantify the one or more vitamin D molecules in the sample based on the image of the detection membrane. In some embodiments provided herein, the imaging device and the programmed computer are a single device.

In some embodiments provided herein, the chase buffer comprises reagents to dissociate the one or more vitamin D molecules from vitamin D binding protein. In some embodiments provided herein, the biological sample is selected from the group consisting of whole blood, serum, plasma, urine, saliva, ocular fluid, spinal fluid, and perspiration.

In some embodiments, the detection antibody comprises a light chain and a heavy chain, wherein the light chain comprises a sequence selected from the group consisting of SEQ ID NOs 1-5 and 16-20; and wherein the heavy chain comprises a sequence selected from the group consisting of SEQ ID NOs 5-15. In some embodiments, the detection antibody exhibits a higher binding affinity to the immunocomplex than the vitamin D binding agent. In some embodiments, the detection antibody comprises a scFv, VH, Fab, or (Fab)2 binding unit.

In some embodiments, the detection antibody comprises a light chain and a heavy chain, wherein the light chain a sequence sharing at least 80% sequence homology to a sequence selected from the group consisting of SEQ ID NOs 1-5, and 16-20, and wherein the heavy chain comprises a sequence having least 80% sequence homology to a sequence selected from the group consisting of SEQ ID NOs 6-15.

In yet another aspect, the present disclosure provides for a method for detecting one or more vitamin D levels in a biological sample with a test device configured to perform a binding assay, comprising: (a) contacting the biological sample to the test device; (b) subjecting the biological sample to the binding assay that utilizes a reaction mixture comprising a complex formed by (1) a vitamin D binding agent and (2) one or more vitamin D molecules; (c) further exposing the complex to a detection agent that binds to an epitope that is formed by complexing the vitamin D binding agent with the one or more vitamin D binding molecules, wherein the binding assay has a sensitivity of detection in the biological sample that is comparable to that of liquid chromatography-tandem mass spectrometry. In some embodiments, the biological sample is selected from the group consisting of whole blood, serum, plasma, urine, saliva, ocular fluid, spinal fluid, and perspiration.

In some embodiments the detection agent comprises a light chain and a heavy chain, wherein the light chain comprises a sequence selected from the group consisting of SEQ ID NOs 1-5 and 16-20, and wherein the heavy chain comprises a sequence selected from the group consisting of SEQ ID NOs 6-15. In some embodiments, the detection agent exhibits a higher binding affinity to the complex than the vitamin D binding agent. In some embodiments, the detection agent comprises a scFv, VH, Fab, or (Fab)2 binding unit.

In some embodiments, the detection agent comprises a light chain and a heavy chain, wherein the light chain comprises a sequence sharing at least 80% sequence homology to a sequence selected from the group consisting of SEQ ID NOs 1-5, and 16-20, and wherein the heavy chain comprises a sequence having least 80% sequence homology to a sequence selected from the group consisting of SEQ ID NOs 6-15.

In some embodiments, the biological sample is selected from the group consisting of whole blood, serum, plasma, urine, saliva, ocular fluid, spinal fluid, and perspiration.

In one aspect, the present invention provides a kit, comprising: any one of the test device disclosed herein; and written instructions for use of the kit. In some embodiments provided herein, the kit further comprises one or more components selected from the group consisting of a sterilization agent; a device to puncture skin; gauze; chase buffer; and a micropipette. In some embodiments provided herein, the sterilization agent is an alcohol wipe. In some embodiments provided herein, the device to puncture skin is selected from the group consisting of a lancet, a needle, and a syringe.

In some embodiments provided herein, the chase buffer is configured to dissociate one or more vitamin D molecules from vitamin D binding protein in a blood sample. In some embodiments provided herein, the kit further comprises a color chart relating signal strength to a quantity of the one or more vitamin D molecules in the sample.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1B provide an exemplary lateral flow device for detecting vitamin D metabolite levels. FIG. 1A displays band densities related to the level of vitamin D metabolites in the subject. FIG. 1B displays a color chart relating the band density to a quantitative range of vitamin metabolite concentration in the blood sample.

DETAILED DESCRIPTION OF THE INVENTION

Figures 1, 1C:
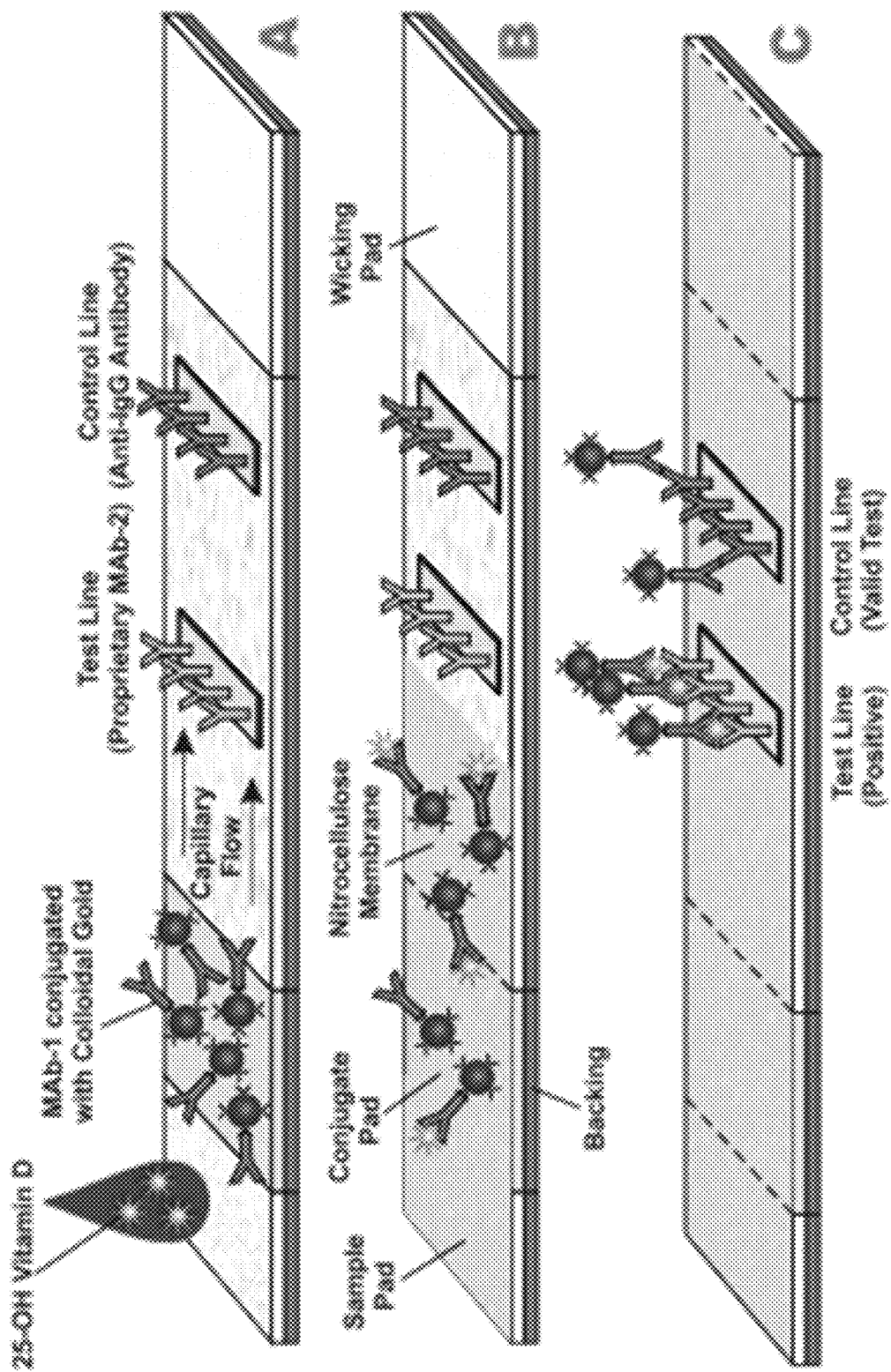
FIG. 1C provides a schematic of an exemplary lateral flow device for detecting vitamin D.

The systems and methods of this disclosure as described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, et al., Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Stryer, L., Biochemistry (4th Ed.) W.H. Freeman, N.Y. (1995); Gait, "Oligonucleotide Synthesis: A Practical Approach" IRL Press, London (1984); Nelson and Cox, Lehninger, Principles of Biochemistry, 3rd Ed., W.H. Freeman Pub., New York (2000); and Berg et al., Biochemistry, 5th Ed., W.H. Freeman Pub., New York (2002), all of which are herein incorporated by reference in their entirety for all purposes.

It is to be understood that this disclosure is not limited to the specific systems and methods, compositions, targets and uses described, as such may, of course, vary. It is also to be understood that the terminology used herein is for the purpose of describing particular aspects only and is not intended to limit the scope of the present disclosure, which will be limited only by appended claims.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide," "nucleic acid," and "oligonucleotide" are used interchangeably. As used herein, they generally refer to a polymeric form of nucleotides of any length, either deoxyribonucleotides or ribonucleotides, or analogs thereof. Polynucleotides may have any three dimensional structure, and may perform any function, known or unknown. Non-limiting examples of polynucleotides are coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

A "control" is an alternative subject or sample used in an experiment for comparison purpose.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny of a biological entity obtained in vivo or cultured in vitro are also encompassed.

The terms "determining", "measuring", "evaluating", "assessing," "assaying," "detecting", and "analyzing" can be used interchangeably herein to refer to any form of measurement, and include determining if an element is present or not (for example, detection). These terms can include both quantitative and/or qualitative determinations. Assessing may be relative or absolute. "Detecting the presence of" can include determining the amount of something present, as well as determining whether it is present or absent.

"Antibody" is an immunoglobulin, or derivative or fragment or active fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

Test Devices

In one aspect, the present disclosure provides for a test device for detecting one or more vitamin D molecules, comprising (a) a housing, contained therein: (i) a sample application unit configured to absorb a biological sample and transport said biological sample to a conjugate pad; (ii) said conjugate pad comprising a first antibody that specifically binds to one or more vitamin D molecules; (iii) a detection zone comprising a first region immobilized therein a second antibody that specifically binds to an immunocomplex, said immunocomplex comprising (a) said first antibody and (b) said one or more vitamin D molecules, or an epitope that is generated by complexing said first antibody and said one or more vitamin D molecules.

"One or more vitamin D molecules" refers to members of the group of fat-soluble secosteriods responsible for enhancing intestinal absorption of calcium, iron, magnesium, phosphate, and zinc. Exemplary members of this group are vitamin $D_1$, vitamin $D_2$, vitamin $D_3$, vitamin $D_4$, and hydroxylated versions thereof. Exemplary hydroxylated vitamin D molecules are 25-hydroxyvitamin $D_2$ (25-OHD$_2$ or 25-(OH)D$_2$) and 25-hydroxyvitamin $D_3$ (25-OHD$_3$ or 25-(OH)D$_3$). One or more vitamin D molecules can include vitamin D compounds with an additional hydroxy group attached at the 1-α position, such as 1,25-hydroxyvitamin $D_3$ (1,25-OHD$_3$, or 1,25-(OH)D$_3$).

The test device can be a lateral flow test device. A lateral flow device can comprise a housing, enclosed therein a test strip. A test strip can comprise a sample application unit, a conjugate pad, and/or a detection unit. A test strip can include one or more materials. If a test strip comprises more than one material, the one or more materials are preferably in fluid communication. One material of a test strip may be overlaid on another material of the test strip, such as for example, filter paper overlaid on nitrocellulose. Alternatively or in addition, a test strip may include a region comprising one or more materials followed by a region comprising one or more different materials. In this case, the regions are in fluid communication and may or may not partially overlap one another. Suitable materials for test strips include, but are not limited to, materials derived from cellulose, such as filter paper, chromatographic paper, nitrocellulose, and cellulose acetate, as well as materials made of glass fibers, nylon, polyethylene terephthalate, polyvinyl chloride, polyacrylamide, cross-linked dextran, agarose, polyacrylate, ceramic materials, and the like. The material or materials of the test strip may optionally be treated to modify their capillary flow characteristics or the characteristics of the applied sample. For example, the sample application region of the test strip may be treated with buffers to correct the pH or specific gravity of an applied urine sample, to ensure optimal test conditions.

The test strip material or materials can be a single structure such as a sheet cut into strips or it can be several strips or particulate material bound to a support or solid surface such as found, for example, in thin-layer chromatography and may have an absorbent pad either as an integral part or in liquid contact. The material can also be a sheet having lanes thereon, capable of spotting to induce lane formation, wherein a separate assay can be conducted in each lane. The material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site. In the following discussion strips will be described by way of illustration and not limitation.

The support for the test strip, where a support is desired or necessary, will generally be water insoluble, frequently non-porous and rigid but may be elastic, usually hydrophobic, and porous and usually will be of the same length and width as the strip but may be larger or smaller. The support material can be transparent, and, when a test device of the present invention is assembled, a transparent support material can be on the side of the test strip that can be viewed by the user, such that the transparent support material forms a protective layer over the test strip where it may be exposed to the external environment, such as by an aperture in the front of a test device. A wide variety of non-mobilizable and non-mobilizable materials, both natural and synthetic, and combinations thereof, may be employed provided only that the support does not interfere with the capillary action of the material or materials, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like. Elastic supports may be made of polyurethane, neoprene, latex, silicone rubber and the like.

The test device can comprise a sample application aperture leading to the sample application unit. In some cases, "sample application aperture" can refer to the portion of a test device or test strip where an opening in the test device provides access to the sample application unit of the test strip. In one embodiment of the present invention, a sample application aperture is created by an open-ended channel at the proximal end of the test device. Preferably, a test strip is engaged in the open-ended channel such that sample contacted with the sample application aperture is thereby applied to the test strip. In an alternate embodiment, a sample application aperture is formed by an opening in the front of a test device, such that the sample application unit of the test strip is in fluid communication with the exterior of the test device.

"Sample application unit" can be the portion of a test strip where sample can be applied. The sample application zone of a test strip of the present invention preferably occurs at the sample application aperture of a test device of the present invention, and is in fluid communication with the sample application aperture. In some cases, the sample application unit comprises a filtering component configured to remove particulate portions of a biological fluid, leaving only the aqueous component. Components for filtering out blood cells, for example, are described in WO2003014726 and WO2009069017, which are hereby incorporated by reference in their entirety.

"Conjugate pad" refers to a region of a test strip where reagent is provided, which can be referred to as a reagent zone. The conjugate pad can be a separate segment of bibulous or non-bibulous material included on the test strip, or it can be a region of a bibulous or non-bibulous material of a test strip that also includes other zones, such as an analyte detection zone. The reagent zone can carry a detection reagent, which may be a direct or indirect label. Preferably the detection reagent is provided in a form that is immobile in the dry state and mobile in the moist state. A reagent can be a specific binding member (e.g., an antibody), an analyte or analyte analog, an enzyme, a substrate, indicators, components of a signal producing system, chemicals or compounds such as buffering agents, reducing agents, chelators, surfactants, etc., that contribute to the function of the test strip assay.

In some cases, a label may be any molecule attached to a specific binding member that can produce a detectable signal. In the present invention, the label may be inert and provide a signal by concentrating in the detection zone, or it may serve solely as a binding site for a member of the signal producing system, or it may spontaneously produce a detectable signal or may produce a detectable signal in conjunction with a signal producing system. A label can be selected from the group consisting of gold particle, latex particle, carbon nanoparticles, selenium nanoparticles, silver nanoparticles, quantum dots, fluorescent compound, textile dyes, enzymes, and liposomes. The label can be gold particle. The label can be latex particle.

"Specific binding member" is one of two different molecules having an area on the surface or in a cavity which specifically binds to and is thereby defined as complementary with a particular spatial and polar organization of the other molecule. Specific binding members can be members of an immunological pair such as antigen-antibody, although other specific binding pairs such as ligand-carrier protein, biotin-avidin, hormone-hormone receptor, nucleic acid duplexes, IgG-protein A, DNA-DNA, DNA-RNA, and the like are not immunological pairs but are included in the definition. A specific binding member can be a binding agent.

A binding agent can be a molecule that complementarily binds one or more molecules. A binding agent can be a protein, a nucleic acid, a ligand, a receptor, or the like.

Exemplary proteins that are binding agents can include hemagglutinins, small molecule binding proteins, active or inactive enzymes or fragmented antibodies. Hemagglutinins can comprise antibodies or lectins. Antibodies can be of one or more classes of immunoglobulins (Ig). For instance, an antibody can be an IgA, IgD, IgE, IgG1, IgG2, IgG3, IgG4, IgM, IgW, or a modified variation thereof. Antibodies can be monoclonal or polyclonal. An antibody can be a humanized antibody, a chimeric antibody, or a bispecific antibody. Antibodies can comprise various types of binding regions. For instance, an antibody can have scFv, VH, Fab, or (Fab)2 binding regions. An antibody can comprise various modifications. For example, an antibody can be modified with one or more detection reagents. An antibody may be conjugated to another binding agent, oligonucleotide or protein.

A binding agent can be a fusion protein that incorporates various combinations of protein subunits. The combinations of protein subunits can be non-naturally occurring or naturally occurring. As a non-limiting example, a fusion protein can incorporate aspects of an antibody (e.g., an Fc region) and one or more receptor domains. A fusion protein can comprise two or more subunits. For example, a fusion protein can be a dimer, trimer, tetramer, or pentamer.

In one aspect of the present invention, one or more binding agents can be used to detect one or more vitamin D molecules. In an embodiment, a vitamin D binding agent specifically binds to one or more vitamin D molecules. A vitamin D binding agent can be a specific binding member. A vitamin D binding agent can be a specific binding member that is capable of binding to one or more vitamin D molecules. A vitamin D binding agent can be a first antibody, as referred to herein.

A detection agent can be used and may bind to a complex of the vitamin D binding agent and one or more vitamin D molecules. A detection agent can be used to detect one or more vitamin D molecules complexed with a vitamin D binding agent or a first antibody. The detection agent can be a detection antibody that specifically binds to a first complex of vitamin D binding agent and a vitamin D molecule. A detection agent can be a second antibody or a detection antibody, as referred to herein.

A third binding agent can be used that is capable of binding to a vitamin D binding agent whether or not the vitamin D binding agent is bound to the one or more vitamin D molecules.

A binding agent may comprise any of the amino acid sequences listed in Table 1 (SEQ ID Nos 1-20), or a combination thereof.

In some embodiments, a conjugate pad comprises a detection reagent, wherein the detection reagent is a first antibody that specifically binds to one or more vitamin D molecules. Vitamin D antibodies are known in the art. An exemplary vitamin D antibody, AF10, was produced as described in Example 1. Other antibodies capable of binding one or more vitamin D molecules are known in the art, such as those described in US20130059825, which is hereby incorporated by reference in its entirety.

A "detection zone" is a region of the test strip in which a dye as described above can be observed to shift location, appear, change color, or optionally to disappear. Detection or observation of the detection zone can be performed by any convenient means, depending upon the choice of detectable label. For example, detection or observation can be performed visually, fluorescently, by reflectance, radiographically, or any other means known the one of ordinary skill in the art.

A detection zone can comprise a first region, immobilized therein a detection agent or second antibody that specifically binds to an immunocomplex comprising (a) the first antibody (e.g., AF10) that specifically binds one or more vitamin D molecules and (b) one or more vitamin D molecules. In some cases, the detection agent or second antibody binds an epitope created when the complex of the vitamin D binding agent or first antibody and one or more vitamin D molecules is formed. For example, a second antibody can bind the junction between the one or more vitamin D molecules and the first antibody. In some cases, the binding of a vitamin D binding agent or first antibody to the one or more vitamin D molecules can cause the formation of an epitope on the vitamin D binding agent or the first antibody that is recognized by the detection agent or second antibody. In some cases the epitope formed upon the binding of one or more vitamin D molecules is not the binding site of the one or more vitamin D molecules, but an epitope at another site of the first antibody. In some cases, the second antibody can recognize the one or more vitamin D molecules when bound to the first antibody. The first region of the detection zone can provide a detectable signal indicating the presence of the analyte. The first region of the detection zone can include an immobilized binding reagent specific for an analyte ("specific binding member"), and/or an enzyme that reacts with the analyte. Other substances that may allow or enhance detection of the analyte, such as substrates, buffers, salts, may also be provided in the detection zone. One or more members of a signal producing system may be bound directly or indirectly to the detection zone. A detection zone can optionally include a second region comprising one or more control zones that provide indication that the test has been performed properly.

In some instances, the detection zone can further comprise a second region. This region can be a control region, immobilized therein a specific binding member that binds the first antibody whether or not it is bound to one or more vitamin D molecules. For example, the specific binding member can be a third antibody can bind the constant region of the first antibody. The third antibody can bind an epitope on the first antibody that is unchanged whether the one or more vitamin D molecules are bound or not. In some cases, the second region can be a control region, and the specific binding member immobilized therein can be protein A. In some cases, the conjugate pad comprises an additional antibody derived from a different species than the first antibody, wherein the additional antibody does not bind the first antibody, vitamin D, or vitamin D binding protein. In some cases, the second region is a control region, and the third antibody recognizes the additional antibody, but does not recognize the first antibody or second antibody. For example, if the first and second antibody are derived from mouse and rat, respectively, the additional antibody can be derived from chicken, and the third antibody can be goat anti-chicken, rat anti-chicken, etc.

Signal appearing in the second region can be used to indicate that the first antibody can be detected and that the test strip is functioning properly. The second region can be a region of a test strip in which a detectable label can be observed to shift location, appear, change color, or optionally to disappear. Detection or observation of the second region may be done by any convenient means, depending upon the particular choice of dye, especially, for example but not limited to, visually, fluorescently, by reflectance, radiographically, by a lateral flow reader and the like.

A biological sample is any material to be tested for the presence or amount of an analyte. Preferably, a biological sample is a fluid sample, preferably a liquid sample. Examples of liquid samples that may be tested using a test device of the present invention include bodily fluids including blood, serum, plasma, saliva, urine, ocular fluid, semen, perspiration, and spinal fluid. The biological sample can be blood or plasma. Viscous liquid, semi-solid, or solid specimens may be used to create liquid solutions, eluates, suspensions, or extracts that can be samples. For example, throat or genital swabs may be suspended in a liquid solution to make a sample.

An exemplary lateral flow assay is provided in FIG. 1C. The exemplary lateral flow assay comprises a sample application pad, conjugate pad, and said detection zone aligned from upstream to downstream along a fluid path along which said biological sample travels. A sample may be applied to the sample application pad or sample pad. Application of a sample may be followed by a chase buffer. From the blood sample, vitamin D (e.g., 25-(OH)D) may flow to a conjugate pad comprising a first antibody (Mab-1) that specifically binds to one or more vitamin D molecules to generate an immunocomplex. A first antibody may be conjugated with a detection reagent, such as colloidal gold. Immunocomplexed and uncomplexed antibody may flow to the detection zone. A detection zone may comprise a control line and a test line. The test line may comprise a second antibody (Mab-2) that specifically binds to an epitope generated by complexing the Mab-1 with one or more 25-(OH)D molecules. Immunocomplexed and non-complexed Mab-1 may laterally flow to a control line comprising a third antibody that is capable of binding to Mab-1 whether or not Mab-1 is bound to one or more vitamin D molecules (Anti-IgG antibody). The uncomplexed and/or immunocomplexed Mab-1 antibody can be detected at the control line. The Mab-2 bound immunocomplexed Mab-1 antibody can be detected at the test line. A level of detection at the test line can be indicative of a level of vitamin D.

Methods

In one aspect, the present disclosure provides methods capable of detecting levels of one or more vitamin D molecules using test devices disclosed herein. The methods can comprise applying a biological sample to the sample application unit of a test device disclosed herein; applying a chase buffer to the sample application unit, and detecting levels of the one or more vitamin D molecules. Such detection can occur by visualizing signal appearing in the second region of the test device, such as by concentration of a labeled first antibody in a detection zone by a specific binding agent.

In some cases, methods further comprise quantifying the one or more vitamin D molecules in the sample. Quantification can be performed by determining a relationship between signal strength in the first region of the detection zone and the amount of analyte present in biological sample. It will be appreciated that the relationship between signal strength and the amount of analyte present in the biological sample may be determined for each batch or each test strip by the application of standards containing known amounts of one or more vitamin D molecules.

In some instances, the quantification will be semi-quantitative, such as by classifying a subject as having sufficient levels, insufficient levels, or deficient levels of one or more vitamin D molecules in the biological sample. Sufficient levels of vitamin D can be at least 10 ng/mL, at least 15 ng/mL, at least 20 ng/mL, at leat 25 ng/mL, at least 30 ng/mL, at least 35 ng/mL, at least 40 ng/mL, or at least 50 ng/mL. Insufficient levels of vitamin D can be at least 5 ng/mL and at most 45 ng/mL, at least 5 ng/mL and at most 40 ng/mL, at least 5 ng/mL and at most 35 ng/mL, at least 5 ng/mL and at most 30 ng/mL, at least 5 ng/mL and at most 25 ng/mL, at least 5 ng/mL and at most 20 ng/mL, at least 5 ng/mL and at most 15 ng/mL, at least 5 ng/mL and at most 10 ng/mL, at least 10 ng/mL and at most 45 ng/mL, at least 10 ng/mL and at most 40 ng/mL, at least 10 ng/mL and at most 35 ng/mL, at least 10 ng/mL and at most 30 ng/mL, at least 10 ng/mL and at most 25 ng/mL, at least 10 ng/mL and at most 20 ng/mL, at least 10 ng/mL and at most 15 ng/mL, at least 15 ng/mL and at most 45 ng/mL, at least 15 ng/mL and at most 40 ng/mL, at least 15 ng/mL and at most 35 ng/mL, at least 15 ng/mL and at most 30 ng/mL, at least 15 ng/mL and at most 25 ng/mL, at least 15 ng/mL and at most 20 ng/mL, at least 20 ng/mL and at most 45 ng/mL, at least 20 ng/mL and at most 40 ng/mL, at least 20 ng/mL and at most 35 ng/mL, at least 20 ng/mL and at most 30 ng/mL, at least 20 ng/mL and at most 25 ng/mL, at least 25 ng/mL and at most 45 ng/mL, at least 25 ng/mL and at most 40 ng/mL, at least 25 ng/mL and at most 35 ng/mL, at least 25 ng/mL and at most 30 ng/mL, at least 30 ng/mL and at most 45 ng/mL, at least 30 ng/mL and at most 40 ng/mL, at least 30 ng/mL and at most 35 ng/mL, at least 35 ng/mL and at most 45 ng/mL, at least 35 ng/mL and at most 40 ng/mL, at least 40 ng/mL and at most 45 ng/mL. Deficient levels of vitamin D can be at most 10 ng/mL, at most 15 ng/mL, at most 20 ng/mL, at leat 25 ng/mL, at most 30 ng/mL, at most 35 ng/mL, at most 40 ng/mL, or at most 50 ng/mL. For example, the subject may have greater than 30 ng/mL of one or more vitamin D molecules and be classified as having sufficient levels of one or more vitamin D molecules. For example, the subject may have between 10-30 ng/mL of one or more vitamin D molecules and be classified as having insufficient levels of one or more vitamin D molecules. For example, the subject may have less than 10 ng/mL of one or more vitamin D molecules and be classified as having deficient levels of one or more vitamin D molecules.

In some instances, quantifying further comprised using an imaging device to produce an image of the detection zone and software on a programmed computer configured to quantify the one or more vitamin D molecules in the biological sample based on the image of the detection zone. The image can be analyzed for signal strength. In some cases, signal strength is compared against the signal strength of the control region to normalize the image for variables such as light intensity, light quality, and variation between imaging devices.

Figure 7:
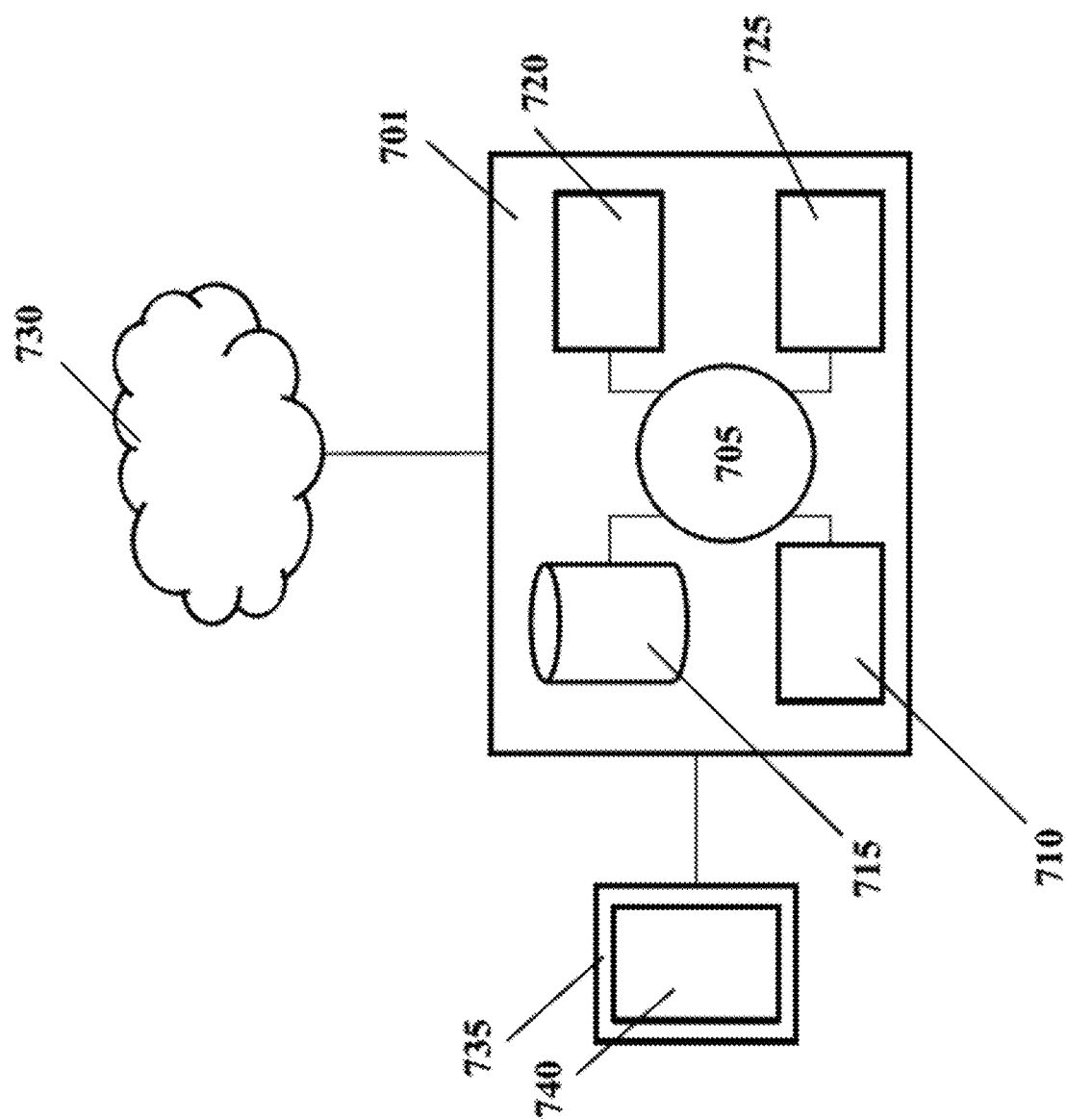
FIG. 7 shows an exemplary computer system that can be used for the analysis of images of the detection zone of the test device disclosed herein.

FIG. 7 shows a computer system 701 that is programmed or otherwise configured to implement methods of the present disclosure. The computer system 701 can be integral to implementing methods provided herein, which would be otherwise extremely difficult to perform in the absence of the computer system 701. The computer system 701 can regulate various aspects of methods of the present disclosure, such as, for example, methods that quantify one or more vitamin D molecules in a biological samples based on an image of a detection zone. The computer system 701 can be an electronic device of a user or a computer system that is remotely located with respect to the electronic device. The electronic device can be a mobile electronic device. As an alternative, the computer system 701 can be a computer server.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 can be a data storage unit (or data repository) for storing data. The computer system 701 can be operatively coupled to a computer network ("network") 730 with the aid of the communication interface 720. The network 730 can be the Internet, an internet and/or extranet, or an intranet and/or extranet that is in communication with the Internet. The network 730 in some cases is a telecommunication and/or data network. The network 730 can include one or more computer servers, which can enable distributed computing, such as cloud computing. The network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. The instructions can be directed to the CPU 705, which can subsequently program or otherwise configure the CPU 705 to implement methods of the present disclosure. Examples of operations performed by the CPU 705 can include fetch, decode, execute, and writeback.

The CPU 705 can be part of a circuit, such as an integrated circuit. One or more other components of the system 701 can be included in the circuit. In some cases, the circuit is an application specific integrated circuit (ASIC).

The storage unit 715 can store files, such as drivers, libraries and saved programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet.

The computer system 701 can communicate with one or more remote computer systems through the network 730. For instance, the computer system 701 can communicate with a remote computer system of a user (e.g., patient, healthcare provider, or service provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The memory 710 can be part of a database. The machine executable or machine readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, genetic information, such as an identification of disease-causing alleles in single individuals or groups of individuals. Examples of UI's include, without limitation, a graphical user interface (GUI) and web-based user interface (or web interface).

A chase buffer may be used to detect one or more vitamin D molecules. The chase buffer can be configured comprise reagents to dissociate the one or more vitamin D molecules from vitamin D binding protein and/or albumin. Non-limiting examples of reagents to dissociate the one or more vitamin D molecules are acidic solution, alkaline solution, 8-anilino-1-napthalenesulfonic acid, 3-(acetonylbenzyl)-4-hydroxycoumarin, alkyl amino fluoro surfactants, perfluorhexanoic acid, perfluoroctanoic acid, proteinase K, urea, and guanidine hydrochloride. For example, the chase buffer can be an acidic solution or an alkaline solution, as described in WO2004063704, which is hereby incorporated by reference in its entirety. In another, the chase buffer can rely on the competitive displacement of Vitamin D from endogenous binding proteins using 8-anilino-1-napthalenesulfonic acid and/or 3-(acetonylbenzyl)-4-hydroxycoumarin, as described in U.S. Pat. No. 7,482,162, which is hereby incorporated by reference in its entirety.

Chase buffer can, for example, be a reagent with a pH from 3.8 to 4.8 and 5-30% DMSO, a liquid organic amide and optionally 0.5-5% of a short chain alcohol, such as described in WO2007039194, which is hereby incorporated by reference in its entirety. Chase buffer can comprise stabilizing agents and capture ligands, including alkyl amino fluoro surfactants as described in WO2008039266, which is hereby incorporated by reference in its entirety.

Kits

In one aspect, the present disclosure provides kits capable of detecting levels of one or more vitamin D molecules comprising test devices disclosed herein and written instructions for the use of the kit. In some instances, kits can further comprise one or more components selected from the group consisting of a sterilization agent, a device to puncture skin, gauze, chase buffer, and a micropipette.

A sterilization agent can be, for example, an alcohol wipe capable of disinfecting human skin.

A device to puncture the skin can be a small, sharp object capable of penetrating the skin of the subject to produce a small volume of blood. The device to puncture the skin can be selected from the group consisting of a lancet, a needle, and a syringe. The lancet can, for example, be spring-powered.

Chase buffer can comprise reagents for dissociating one or more vitamin D molecules from vitamin D binding protein, as described previously.

A micropipette can provide a known volume of biological sample to the device.

The kit can further comprise a color chart relating signal strength to a quantity of said one or more vitamin D molecules in a sample. Due to potential batch-to-batch variability, the color chart can be generated empirically for each batch of test devices by running standards containing known amounts of one or more vitamin D molecules and determining the colors corresponding to different ranges of amounts of one or more vitamin D molecules in the biological sample.

EXAMPLES

Example 1

Generation of Monoclonal Antibody to 25-(OH)D

Monoclonal antibodies against 25-(OH)D were prepared by a modified method of Kohler and Milstein (G. Kohler and C. Milstein Nature, 1975, 256, 495). Mice were immunized by subcutaneous injection of 25-(OH)D conjugated at its 3-position to carrier protein KHL. The complete Freund's adjuvant was injected with the antigen. The incomplete Freund's adjuvant was used for antigen boosts. The immune response was monitored by ELISA against 25-(OH)$D_3$. After four to five antigen boosts, the spleen cells were harvested and fused with myeloma cells in the presence of polyethylene glycol (PEG). The fused cells were seeded in 96-well plates and grown in the presence of selective hypoxanthine, aminopterin and thymidine (HAT) medium. The supernatants from the fused cells were tested by ELISA for binding activity to 25-(OH)$D_3$ and 25-(OH)$D_2$. The clone AF10, which has a high affinity for binding both 25-(OH)$D_3$ and 25-(OH)$D_2$, was selected for large scale of antibody production and purification.

Example 2

Generation of a Monoclonal Antibody Against an Immunocomplex of 25-(OH)D and mAb From Immunized Mice Mice were immunized by subcutaneous injection of 25-(OH)D conjugated at its 26-position to carrier protein keyhole limpet hemocyanin (KLH). The complete Freund's adjuvant was injected with antigen. KLH conjugate and the incomplete Freund's adjuvant was used for the first and third boosts, and the immunocomplex of 25-(OH)D:antibody AF10 was used for the second and fourth boosts. The immune response was monitored by ELISA assay to the immunocomplex of 25-(OH)D:antibody AF10. After 4 boosts, the spleen cells were harvested. The RNA from the spleen cells was then isolated and variable gene amplification was performed.

The mRNA was isolated by using Dynabeads® mRNA Purification Kit (ThermoFisher) according to the manufacturer's protocol. Subsequently, first strand cDNA was generated using Superscript II reverse transcriptase (Invitrogen, Carlsbad, Calif.). From the cDNA, heavy and light chain variable genes were amplified separately by PCR using primer sets for mouse VH, VK and Vλ, as described according to Phage Display: A Laboratory Manual (Cold Spring Harbor Laboratory Press). Heavy and light chain variable region genes were further amplified by PCR to add partial sequence of $(G5S)_4$ linker to the 3' VH and 5' VL. In the third PCR reaction, an equal amount of second round amplified VH and VL DNA was mixed for single-chain variable fragment (scFv) assembly. The final scFv DNA was purified with Qiagen PCR purification column (QIAGEN Inc., Germany). The purified scFv DNA and PCANTABA5 vector DNA were digested with restriction enzymes NcoI and NotI (New England Lab) and then size-selected by 1% agarose gel. Excised bands were purified with the QIA-QUICK® Gel Extraction Kit. Digested scFv, vector DNA and T4 ligase (New England Lab) were mixed for overnight ligation at 16° C. 20 µg of ligated DNA was purified and transformed into *E coli* TG1 competent cells by electroporation. After transformation, TG1 cells were suspended into SOC medium and incubated for 1 h at 37° C. and 250 rpm shaking. The TG1 cells were plated on 2YT-agar plates containing 100 µg/ml of carbenicillin and 2% glucose. Following overnight 30° C. incubation, the TG1 transformants were harvested into 2YT containing 15% glycerol, 100 µg/ml of carbenicillin and 2% glucose, and the library aliquots were kept at −80° C. for storage. This procedure resulted in a library size of $1.2 \times 10^9$ colonies.

Phage displayed library was prepared as follows. 200 mL 2YT medium (with 100 µg/ml of carbenicillin and 2% glucose) was inoculated with library TG1 cells at starting OD 0.1. After 3-4 hours of incubation at 37° C. with 250 rpm shaking, KO7 helper phage was added at a 1:10 ratio of cells to phage, and the culture was incubated at 37° C. for 1 hour without sharking. The TG1 cells were centrifuged and the cell pellet was re-suspended into 2 L of 2YT with 100 µg/ml carbenicillin and 35 µg/ml Kanamycin, followed by overnight incubation at 30° C. with 250 rpm sharking. TG1cells were then centrifuged for 30 minutes at 6000×g at 4° C. The library phage particles were purified by PEG-precipitation from culture supernatant, resuspended into phosphate-buffered saline (PBS) and titered by OD268 measurement. The phage display antibody library was stored at −80° C. in PBS with 20% glycerol.

Immunocomplex-specific antibodies were selected from the above mouse scFv phage display library by the following selection procedure. The microtiter well was coated with 1 µg of mAb AF10 overnight at 4° C. After 2 hour blocking with 1× CHEMIBLOCKER® (EMD Millipore), 1 µg of 25-(OH)D$_3$ was added to each well for overnight incubation at 4° C. The well was washed 3 times with PBS and blocked with 1× CHEMIBLOCKER® for 1 hour at room temperature. Prior to performing affinity selection against the immunocomplex of 25-(OH)D:antibody AF10, 400 µl of the phage library solution (a total of 1,012 phage particles) was pre-incubated in a well containing antibody AF10 without vitamin D for 2 hours at room temperature, after which the unbound phages were transferred into 4 wells with the immunocomplex of 25-(OH)D:antibody AF10 for 2 hour incubation at room temperature. The unbound phages were removed and the well was washed 10 times with PBS-TWEEN®. Bound phages were eluted with 100 µl of 100 mM HCl for 10 minutes, and eluted phages were harvested and neutralized with 10% 1 M Tris-HCl. The eluted phages were then added to 10 mL of fresh TG1 cells (OD600≈0.8) for 1 hour incubation at 37° C. Infected TG1 cells were plated on two 2YT plates with carbenicillin and glucose for overnight growth, and overnight cells were harvested for first round phage preparation as described above. The affinity selection procedure was performed on these second round phages as just described. A total of three rounds of affinity selection were performed.

The infected TG1 colonies from the third round of affinity selection were picked for expression of scFv-p3 fusion and confirmation of binding activity. Briefly, isolated TG colonies were picked into 96 well plates (5 plates and a total of 480 colonies) with 100 µl of 2YT/carbenicillin and glucose, and incubated overnight at 30° C. The second day, 10 µl of culture per well was transferred into a corresponding well in a 96-well deep plate containing 500 µl per well 2YT medium containing carbenicillin and 0.1% Glucose. The deep-well plates were incubated in a 37° C. shaker incubator shaking at 250 rpm until the cultures reach OD600 of 0.8-1. 100 µl of 2YT containing 6 mM IPTG was then added to each well and the expression plate was incubated overnight at 30° C. shaking at 250 rpm. 160 µL of lysis buffer containing 2.5 mg/mL lysozyme and 5 mM EDTA were then added to each well of the expression plate, and the cultures were shaken for 1 h at room temperature. The culture supernatant was mixed with 140 µl 2×CHEMIBLOCKER® per well and incubated for an additional 30 min while shaking at 250 rpm. The culture supernatants were centrifuged and prepared for binding assay as below.

Figure 2:
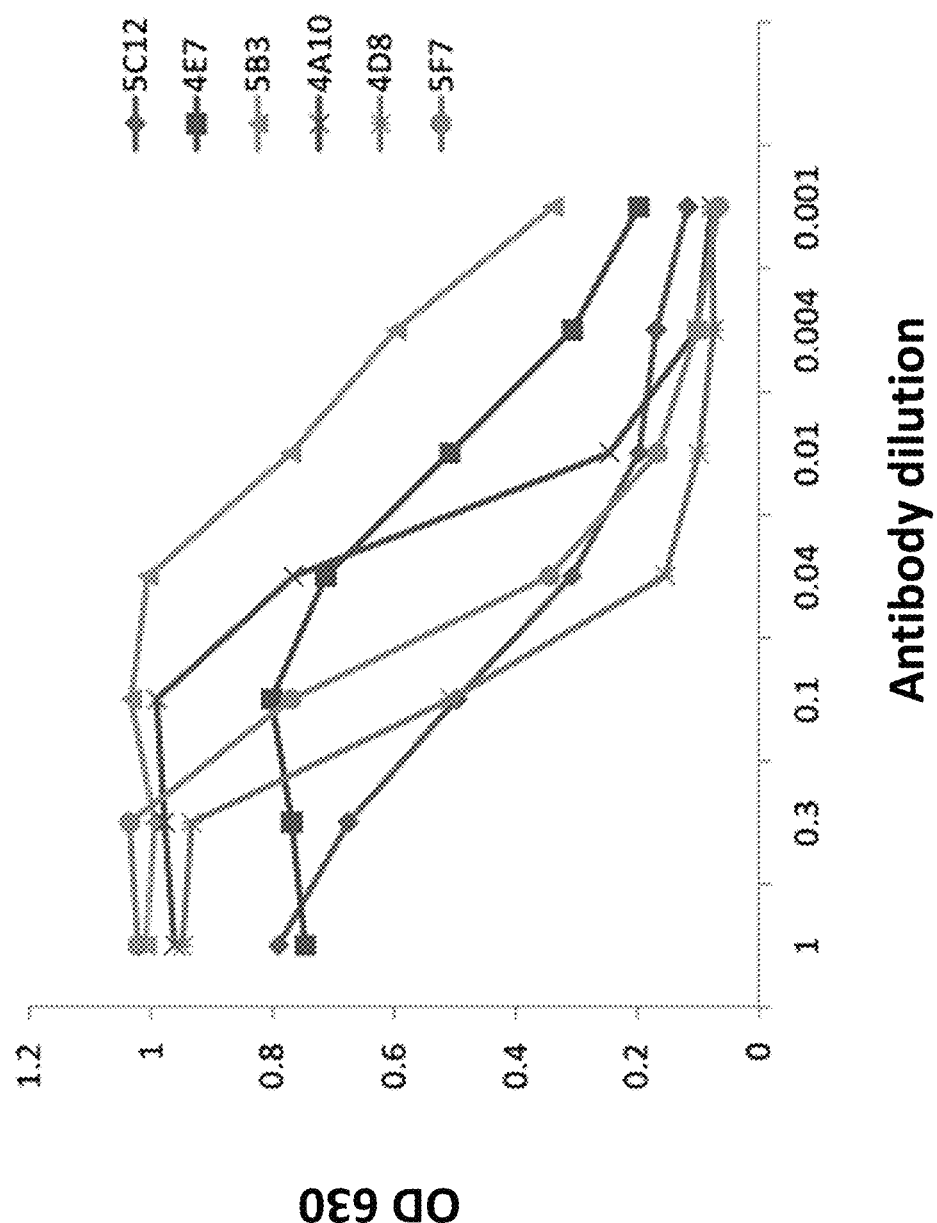
FIG. 2 illustrates the results of an enzyme-linked immunosorbent assay (ELISA) to test the binding of mouse antibody clones to the 25-(OH)$D_3$:AF10 antibody immunocomplex.

To screen for the clones capable of binding the immunocomplex of 25-(OH)D:antibody AF10, two 96-well assay plates were prepared for each expression plate, one plate coated with AF10 antibody only, the other coated with the immunocomplex of 25-(OH)D:antibody AF10. The assay plates were blocked with 1× CHEMIBLOCKER® for 2 hours at room temperature. The culture supernatants from the expression plate were transferred to the corresponding well of the assay plate. After 1 hour incubation at room temperature and three PBS-TWEEN®washes, 100 µL of mouse anti-M13 p3 antibody (New England Lab) was added to each well for 1 hour incubation at room temperature. The samples were washed three times with PBS-TWEEN®, and 100 µL of horse radish peroxidase (HRP)-conjugated goat anti-mouse IgG was added to each well for 1 hour incubation. The samples were washed three times with PBS-TWEEN®, and 100 µL of substrate 3,3',5,5'-Tetramethylbenzidine (TMB) was added to each well. The OD630 was measured after 10-30 minutes development. The clones that bound to the immunocomplex of 25-(OH)D:antibody AF10, but not AF10 antibody alone, were selected for confirmation. The positive culture supernatants were serially diluted in a 1:3 ratio and were assayed again following the above procedure. FIG. 2 shows six clones with binding activity to the immunocomplex of 25-(OH)D$_3$:antibody AF10. The unique sequences of the heavy chain variable regions (SEQ ID NOs 6-15) and light chain variable regions (SEQ ID NOs 1-5 and 16-20) are listed in TABLE 1.

A light chain can comprise a sequence selected from the group consisting of SEQ ID NOs 1-5, and 16-20. A heavy chain can comprise a sequence selected from the group consisting of SEQ ID NOs 6-15. In some instances, the light chain can comprise a sequence sharing at least 80% sequence homology to a sequence selected from the group consisting of SEQ ID NOs 1-5, and 16-20. In some instances, the heavy chain can comprise a sequence having least 80% sequence homology to a sequence selected from the group consisting of SEQ ID NOs 6-15.

An antibody may comprise light chain CDR and said heavy chain CDR with any of the following amino acid sequences: a heavy chain of SEQ ID NO 6 and a light chain of SEQ ID NO 1, a heavy chain of SEQ ID NO 6 and a light chain of SEQ ID NO 2, a heavy chain of SEQ ID NO 6 and a light chain of SEQ ID NO 3, a heavy chain of SEQ ID NO 6 and a light chain of SEQ ID NO 4, a heavy chain of SEQ ID NO 6 and a light chain of SEQ ID NO 5, a heavy chain of SEQ ID NO 6 and a light chain of SEQ ID NO 16, a heavy chain of SEQ ID NO 6 and a light chain of SEQ ID NO 17, a heavy chain of SEQ ID NO 6 and a light chain of SEQ ID NO 18, a heavy chain of SEQ ID NO 6 and a light chain of SEQ ID NO 19, a heavy chain of SEQ ID NO 6 and a light chain of SEQ ID NO 20.

An antibody may comprise light chain CDR and said heavy chain CDR with any of the following amino acid sequences a heavy chain of SEQ ID NO 7 and a light chain of SEQ ID NO 1, a heavy chain of SEQ ID NO 7 and a light chain of SEQ ID NO 2, a heavy chain of SEQ ID NO 7 and a light chain of SEQ ID NO 3, a heavy chain of SEQ ID NO 7 and a light chain of SEQ ID NO 4, a heavy chain of SEQ ID NO 7 and a light chain of SEQ ID NO 5, a heavy chain of SEQ ID NO 7 and a light chain of SEQ ID NO 16, a heavy chain of SEQ ID NO 7 and a light chain of SEQ ID NO 17, a heavy chain of SEQ ID NO 7 and a light chain of SEQ ID NO 18, a heavy chain of SEQ ID NO 7 and a light chain of SEQ ID NO 19, a heavy chain of SEQ ID NO 7 and a light chain of SEQ ID NO 20.

An antibody may comprise light chain CDR and said heavy chain CDR with any of the following amino acid sequences: a heavy chain of SEQ ID NO 8 and a light chain of SEQ ID NO 1, a heavy chain of SEQ ID NO 8 and a light chain of SEQ ID NO 2, a heavy chain of SEQ ID NO 8 and a light chain of SEQ ID NO 3, a heavy chain of SEQ ID NO 8 and a light chain of SEQ ID NO 4, a heavy chain of SEQ ID NO 8 and a light chain of SEQ ID NO 5, a heavy chain of SEQ ID NO 8 and a light chain of SEQ ID NO 16, a heavy chain of SEQ ID NO 8 and a light chain of SEQ ID NO 17, a heavy chain of SEQ ID NO 8 and a light chain of SEQ ID NO 18, a heavy chain of SEQ ID NO 8 and a light chain of SEQ ID NO 19, a heavy chain of SEQ ID NO 8 and a light chain of SEQ ID NO 20.

An antibody may comprise light chain CDR and said heavy chain CDR with any of the following amino acid sequences: a heavy chain of SEQ ID NO 9 and a light chain of SEQ ID NO 1, a heavy chain of SEQ ID NO 9 and a light chain of SEQ ID NO 2, a heavy chain of SEQ ID NO 9 and a light chain of SEQ ID NO 3, a heavy chain of SEQ ID NO 9 and a light chain of SEQ ID NO 4, a heavy chain of SEQ ID NO 9 and a light chain of SEQ ID NO 5, a heavy chain of SEQ ID NO 9 and a light chain of SEQ ID NO 16, a heavy chain of SEQ ID NO 9 and a light chain of SEQ ID NO 17, a heavy chain of SEQ ID NO 9 and a light chain of SEQ ID NO 18, a heavy chain of SEQ ID NO 9 and a light chain of SEQ ID NO 19, a heavy chain of SEQ ID NO 9 and a light chain of SEQ ID NO 20.

An antibody may comprise light chain CDR and said heavy chain CDR with any of the following amino acid sequences: a heavy chain of SEQ ID NO 10 and a light chain of SEQ ID NO 1, a heavy chain of SEQ ID NO 10 and a light chain of SEQ ID NO 2, a heavy chain of SEQ ID NO 10 and a light chain of SEQ ID NO 3, a heavy chain of SEQ ID NO 10 and a light chain of SEQ ID NO 4, a heavy chain of SEQ ID NO 10 and a light chain of SEQ ID NO 5, a heavy chain of SEQ ID NO 10 and a light chain of SEQ ID NO 16, a heavy chain of SEQ ID NO 10 and a light chain of SEQ ID NO 17, a heavy chain of SEQ ID NO 10 and a light chain of SEQ ID NO 18, a heavy chain of SEQ ID NO 10 and a light chain of SEQ ID NO 19, a heavy chain of SEQ ID NO 10 and a light chain of SEQ ID NO 20.

An antibody may comprise light chain CDR and said heavy chain CDR with any of the following amino acid sequences: a heavy chain of SEQ ID NO 11 and a light chain of SEQ ID NO 1, a heavy chain of SEQ ID NO 11 and a light chain of SEQ ID NO 2, a heavy chain of SEQ ID NO 11 and a light chain of SEQ ID NO 3, a heavy chain of SEQ ID NO 11 and a light chain of SEQ ID NO 4, a heavy chain of SEQ ID NO 11 and a light chain of SEQ ID NO 5, a heavy chain of SEQ ID NO 11 and a light chain of SEQ ID NO 16, a heavy chain of SEQ ID NO 11 and a light chain of SEQ ID NO 17, a heavy chain of SEQ ID NO 11 and a light chain of SEQ ID NO 18, a heavy chain of SEQ ID NO 11 and a light chain of SEQ ID NO 19, a heavy chain of SEQ ID NO 11 and a light chain of SEQ ID NO 20.

An antibody may comprise light chain CDR and said heavy chain CDR with any of the following amino acid sequences: a heavy chain of SEQ ID NO 12 and a light chain of SEQ ID NO 1, a heavy chain of SEQ ID NO 12 and a light chain of SEQ ID NO 2, a heavy chain of SEQ ID NO 12 and a light chain of SEQ ID NO 3, a heavy chain of SEQ ID NO 12 and a light chain of SEQ ID NO 4, a heavy chain of SEQ ID NO 12 and a light chain of SEQ ID NO 5, a heavy chain of SEQ ID NO 12 and a light chain of SEQ ID NO 16, a heavy chain of SEQ ID NO 12 and a light chain of SEQ ID NO 17, a heavy chain of SEQ ID NO 12 and a light chain of SEQ ID NO 18, a heavy chain of SEQ ID NO 12 and a light chain of SEQ ID NO 19, a heavy chain of SEQ ID NO 12 and a light chain of SEQ ID NO 20.

An antibody may comprise light chain CDR and said heavy chain CDR with any of the following amino acid sequences: a heavy chain of SEQ ID NO 13 and a light chain of SEQ ID NO 1, a heavy chain of SEQ ID NO 13 and a light chain of SEQ ID NO 2, a heavy chain of SEQ ID NO 13 and a light chain of SEQ ID NO 3, a heavy chain of SEQ ID NO 13 and a light chain of SEQ ID NO 4, a heavy chain of SEQ ID NO 13 and a light chain of SEQ ID NO 5, a heavy chain of SEQ ID NO 13 and a light chain of SEQ ID NO 16, a heavy chain of SEQ ID NO 13 and a light chain of SEQ ID NO 17, a heavy chain of SEQ ID NO 13 and a light chain of SEQ ID NO 18, a heavy chain of SEQ ID NO 13 and a light chain of SEQ ID NO 19, a heavy chain of SEQ ID NO 13 and a light chain of SEQ ID NO 20.

An antibody may comprise light chain CDR and said heavy chain CDR with any of the following amino acid sequences: a heavy chain of SEQ ID NO 14 and a light chain of SEQ ID NO 1, a heavy chain of SEQ ID NO 14 and a light chain of SEQ ID NO 2, a heavy chain of SEQ ID NO 14 and a light chain of SEQ ID NO 3, a heavy chain of SEQ ID NO 14 and a light chain of SEQ ID NO 4, a heavy chain of SEQ ID NO 14 and a light chain of SEQ ID NO 5, a heavy chain of SEQ ID NO 14 and a light chain of SEQ ID NO 16, a heavy chain of SEQ ID NO 14 and a light chain of SEQ ID NO 17, a heavy chain of SEQ ID NO 14 and a light chain of SEQ ID NO 18, a heavy chain of SEQ ID NO 14 and a light chain of SEQ ID NO 19, a heavy chain of SEQ ID NO 14 and a light chain of SEQ ID NO 20.

An antibody may comprise light chain CDR and said heavy chain CDR with any of the following amino acid sequences: a heavy chain of SEQ ID NO 15 and a light chain of SEQ ID NO 1, a heavy chain of SEQ ID NO 15 and a light chain of SEQ ID NO 2, a heavy chain of SEQ ID NO 15 and a light chain of SEQ ID NO 3, a heavy chain of SEQ ID NO 15 and a light chain of SEQ ID NO 4, a heavy chain of SEQ ID NO 15 and a light chain of SEQ ID NO 5, a heavy chain of SEQ ID NO 15 and a light chain of SEQ ID NO 16, a heavy chain of SEQ ID NO 15 and a light chain of SEQ ID NO 17, a heavy chain of SEQ ID NO 15 and a light chain of SEQ ID NO 18, a heavy chain of SEQ ID NO 15 and a light chain of SEQ ID NO 19, a heavy chain of SEQ ID NO 15 and a light chain of SEQ ID NO 20.

TABLE 1

Exemplary heavy and light chain variable regions

| Sequence No. | Amino acid sequences |
|---|---|
| 1 | DIQMTQSPAIMSASPGEKVTITCSASSSVSYMHWYQQKSGTSPK LWIYSTSNLASGVPARFSGSGSGTSYSLTISSMEAEDAATYYCQQ RSSYPYTFGGGTKLEIK |
| 2 | DIVLTQSQKFMSTSVGDRVSVTCKASQNVGTNVAWYQQKPGQS PKALIYSASYRYSGVPDRFTGSGSGTDFTLTISNVQSEDLAEYFC QQHYSTPYTFGGGTKLEIK |
| 3 | DIVLTQSPASLAVSLGQRATISCRASKSVSTSGYSYMHWYQQKP GQPPKLLIYLASNLESGVPARFSGSGSGTDFTLNIHPVEEEDAAT YYCQQSNEDPFTFGSGTKLELK |
| 4 | DIVLTQSPSSLSASLGERVSLTCRASQDIGSSLNWLQQEPDGTIKR LIYATSSLDSGVPKRFSGSRSGSDYSLTISSLESEDFVDYYCQQHG ESPLTFGAGTKLEIK |
| 5 | DIVMTQSHKFMSTSVGDRVSITCKASQDVGTAVAWYQQKPGQS PKLLIYWASTRHTGVPDRFTGSGSGTDFTLTISNVQSEDLADYFC QQYASSPYTFGGGTKLEIK |
| 6 | EVQLQQSGAELAKPGASVKMSCKASGYTFTSYWMHWVKQRPG QGLEWIGYINPSTGYTEYNQKFKDKATLTADKSSSTAYMQLSSL TSEDSVVYYCARQDGYYVGYFDYWGQGTTLTVSS |
| 7 | EVELQESGAELVRPGASVKLSCKASGYSFTNYWMNWVRQRPG QGFEWIGEINPSNGDTFYNQKFKGKATLIVDKSSSTAYMELLSLT SEDSAVYYCARIGGYYFDYWGQGTTLTVSS |
| 8 | EVNVVESGAELVKPGASVRLSCTTSGFNIEDSYIHWVKQRPEQG LEWIGRIDPANGNIKSDPKFQGKATISADTSSNTAYLQLSSLTSED TAVYYCLYYYDSSDYWGQGTTLTVSS |
| 9 | EVKLVESGPELEKPGASVKISCKASGYSFTGYNMNWVKQSNGK SLEWIGNIDPYYGGTSYNQKFKGKATLTVDKSSSTAYMQLKSLT SEDSAVYYCARWSYYGNYVYWYFDVWGAGTTLTVSS |
| 10 | EVQLQQSGAELVRSGASVKLSCTASGFNIKDYYMHWVKQRPEQ GLEWIGRIDPANGNTKYDPKFQGKATITADTSSNTAYLQLSSLTS EDTAVYYCARSYYFDYWGQGTTLTVSS |
| 11 | EVQLLESGGGLVQPGGSLRLSCAASGFTFSSYTVNWVRQAPGK GLEWLSVISGDGSNTYYADSVKGRFTISRDNSKNTLYLQMNSLR AEDTAVYYCAKALNAGWGFDYWGQGTLVTVSS |
| 12 | QVQLLESGGGLVKPGGSLRLSCAASGFTFSGSAMHWVRQAPGK GMEWVSAISGSGGSTYYADSMKGRFTISRDNSKNTLYLQMNSL RAEDTAVYYCARNGYTDGYGMDYWGQGTLVTVSS |
| 13 | EVQLLESGGGLVQPGGSLRLSCAASGFTFSDSSVNWVRQAPGK GLEWLAVISGDGGSTYYADSVKGRVTISRDNSKNTLYLQMNSL RAEDTAVYYCARAIFPSYMDVWGQGTLVTVSS |
| 14 | EVQLVQSGPEVKKPGTSVKVSCKASGFTFTSSAVDWVRQARGQ RLEWIGWIVVGSGNTSYAQKFQERVTITRDMSTSTAYMELSSLR SEDTAVYYCAKSVTYYYMDHWGQGTLVTVSS |
| 15 | QVQLVQSGAEVKKPGSSVKVSCKASGGTFNSYAISWVRQAPGQ GLEWMGVIIGIFGTATYAQSVQGRVTITADESTSTAYMELSSLRS EDTAVYYCARSGRYSRSFDVWGQGTLVTVSS |
| 16 | EIVLTQSPGTLSLSPGERATLSCRANRLVSSSMLAWYQQKPGQA PRLLIGASKRATGIPDRFSGSGSGTDFTLTISRLEPEDFAVYYCAQ YDGSSYTFGQGTKLEIKR |
| 17 | QSVLTQPPSVSGSPGQRVTISCTGNNLSGYYVSWYQQLPGTAPK LLIYGNSNRPSGVPDRFSGSKSGTSASLAITGLQAMDEADYYCA AYYSGTYVFGQGTKLTVLGQ |

TABLE 1-continued

Exemplary heavy and light chain variable regions

| Sequence No. | Amino acid sequences |
|---|---|
| 18 | SYELTQPLSVSVSLGQTARITCWDNVGGYNVHWYQQKPGQSPV
LVIYRDSERPSGIPERFSGSNSGNTATLTISRAQAGDEADYYCSSY
YQSTVLFGGGTKLTVLGQ |
| 19 | DIQMTQSPSSLSASVGDRVTITCQASNVGGNYLNWYQQKPGKA
PKLLIYDASNLETGVPSRFSGSGSGTDFTFTISSLQPEDIATYYCS
AYHQSTYTFGQGTKVEIKR |
| 20 | DIQMTQSPSSLSASVGDRVTITCRASKVGSSYVNWYQQKPGKAP
KLLIYAASSLESGVPSRFSGSGSGTDFTLTISSLQPEDFATYYCAS
YYSTSTFGGGTKVEIKR |

Example 3

Generation of a Monoclonal Antibody to the Immunocomplex of 25-(OH)D:mAB From a Synthetic Library The synthetic antibody library was designed based on the natural VH/VL pairing frequency (described in Protein Engineering, Design & Selection pp. 1-7, 2012 doi:10.1093/protein/gzs043), the frameworks of frequently paired human VH1, VH3, VK1, VK3, Vλ1, Vλ2 and Vλ3 were selected as master genes for gene synthesis. The selected master genes were synthesized by PCR assembly of overlapping oligos. The length of oligos was between 60 and 80 bases, and the oligos for all CDRs were degenerate oligos using the nucleotides NNS and/or MVS to randomize amino acid residues. After the first round of PCR assembly, 5 light chain master genes were assembled with a light chain constant region by PCR. The resulting full-length light chain genes were digested with restriction enzymes HindIII and NcoI (New England Lab) and size-selected on a 1% agarose gel. The size-selected fragments were purified and extracted with the QIAQUICK® Gel Extraction Kit. Digested light chain genes, pAXD20 vector DNA, and T4 ligase (New England Lab) were mixed and ligation was allowed to proceed overnight at 16° C. For each light chain gene construct, 20 μg of ligated DNA was purified and transformed into E coli TOP10 competent cells by electroporation. Transformants were then grown on 100 2YT-agar plates containing 100 μg/ml of carbenicillin and 2% glucose. After overnight 30° C. incubation, library transformants were harvested and suspended in 2YT with 15% glycerol. Half of the stock was stored as library aliquots at −80° C., and the rest was processed by Qiagen Maxiprep kit. The resulted library size is listed in Table 2. The DNA of AFK1 and AFk3 were combined, and AFL1, AFL2 and AFL3 were also combined for the next step of heavy chain cloning.

TABLE 2

Characteristics of light chain libraries

| Library | Library size |
|---|---|
| AFK1 | $1.1 \times 10^9$ |
| AFK3 | $1.2 \times 10^9$ |
| AFL1 | $8.5 \times 10^8$ |
| AFL2 | $7.6 \times 10^8$ |
| AFL3 | $8 \times 10^8$ |

PCR assembled VH1 and VH3 master genes were further assembled with CH1 constant region by PCR, the resulting Fd genes were digested with restriction enzymes NcoI and SalI (New England BioLab) and size-selected by 1% agarose gel. The size-selected fragment was purified and extracted with the QIAQUICK® Gel Extraction Kit. Digested Fd genes, light chain library DNA and T4 ligase (New England Lab) were mixed and ligation was allowed to proceed overnight at 16° C. For each Fd chain gene library, 40 μg of ligated DNA was purified and transformed into E. coli TG1 competent cells by electroporation. Transformants were then grown on 400 2YT-agar plates containing 100 μg/ml of carbenicillin and 2% glucose. After overnight 30° C. incubation, library transformants were harvested and suspended in 2YT with 15% glycerol. Library aliquots were prepared and stored at −80° C. The resulting library sizes are listed in Table 3.

TABLE 3

Characteristics of phage display libraries

| Library | Library size |
|---|---|
| AFH1K | $3.6 \times 10^9$ |
| AFH3K | $3.3 \times 10^9$ |
| AFH1L | $3.5 \times 10^9$ |
| AFH3L | $3.2 \times 10^9$ |
| Total | $1.4 \times 10^{10}$ |

Phage display libraries were prepared in the following manner. A 500 2YT (with 100 μg/ml of carbenicillin and 2% glucose) culture was inoculated with library TG1 cells at a starting OD of 0.1. After 3-4 hours incubation at 37° C. with 250 rpm shaking, KO7 helper phage was added in a 1:10 ratio. The culture was then incubated at 37° C. for 1 hour without shaking. The TG1 cells were centrifuged and the cell pellet was re-suspended into 2 L of 2YT containing 100 μg/ml carbenicillin and 35 μg/ml Kanamycin for overnight incubation at 30° C. with 250 rpm shaking. TG1cells were then centrifuged for 30 min at 6000× g at 4° C. The library phage particles were purified by PEG-precipitation from culture supernatants, resuspended into PBS and titered by OD268 measurement. The phage display antibody library was stored at −80° C. in PBS with 20% glycerol. Each library was prepared separately and kept separately.

The procedure to select immunocomplex-specific antibodies is similar to the description in the Example 2. Briefly, two kinds of microtiter wells were prepared, one coated with AF10 antibody only, and the second with the immunocomplex of 25-(OH)D$_3$:AF10. Before affinity selection, the individual library was pre-incubated in AF10-only wells for to deplete for phages that bind AF10 alone. The supernatant is then transferred to the microtiter wells coated with the immunocomplex of 25-(OH)D$_3$:AF10. In the first round affinity selection, a total of eight wells were used, and each library phage was added to two wells. In the second round of affinity selection, the phages from first round were mixed and 4 wells were used for incubation. A total of three rounds of affinity selection were performed.

The colonies from the third round of affinity selection were picked for expression of p3 fusion and confirmation of binding activity. The procedure is similar to that described in Example 2. Briefly, five 96-well plates and a total of 480 colonies were picked to make master plates. During the second day, 10 μl of culture per well was transferred into a corresponding well in a 96-well deep-well expression plate. The deep-well plates were incubated in a 37° C. shaker incubator with shaking at 250 rpm until the cultures reach OD600 nm of 0.8–1. 100 μl of 2YT containing 6 mM IPTG was added to each well, and the expression plate was incubated overnight at 30° C. while shaking at 250 rpm. 160 μl of lysis buffer containing 2.5 mg/ml lysozyme and 5 mM EDTA was added to each well of the expression plate, and the plate was incubated with shaking for 1 hour at room temperature. The culture supernatant was mixed with 140 μl 2×CHEMIBLOCKER®per well and incubated for an additional 30 min at 250 rpm. The culture supernatants were centrifuged and prepared for binding assay as below.

Figure 3:
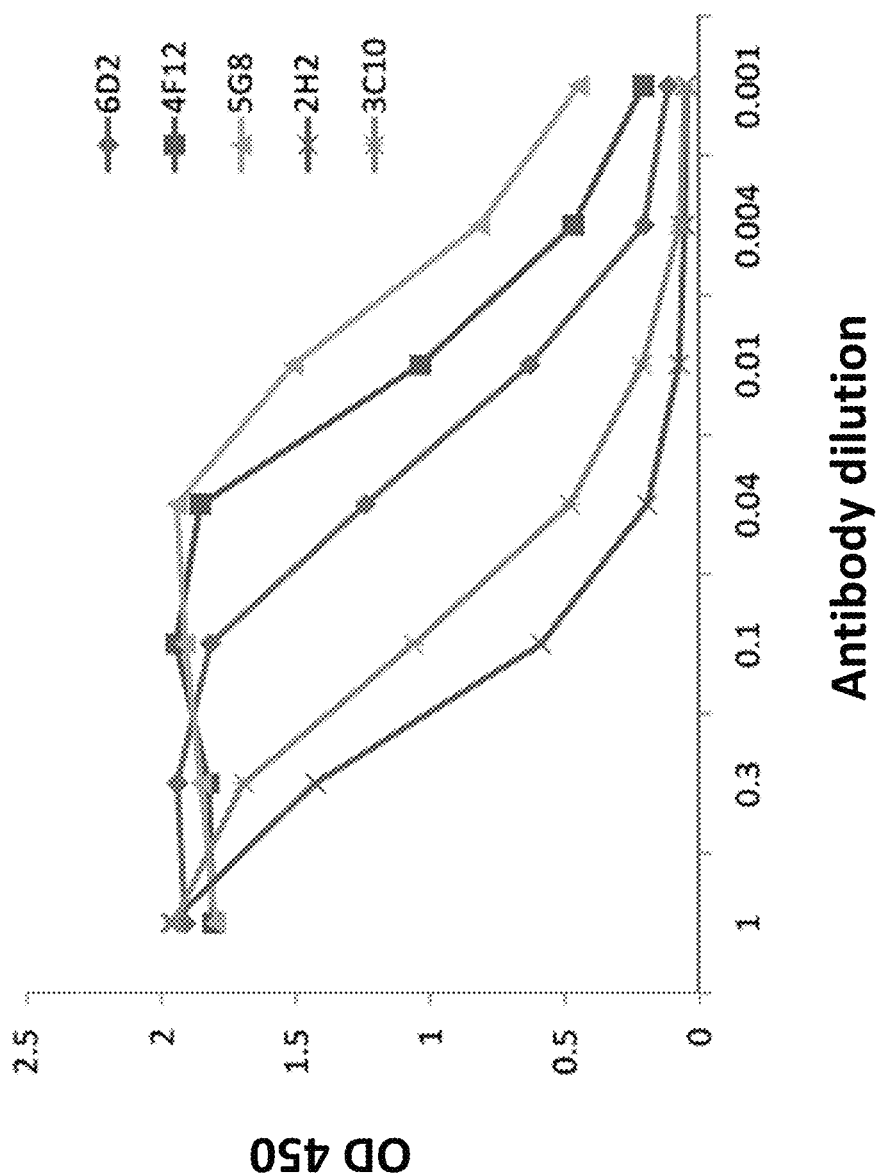
FIG. 3 illustrates the results of an ELISA testing the binding of synthetic antibody clones to the immunocomplex of 25-(OH)$D_3$:AF10 antibody.

The ELISA screening procedure was similar to that described in Example 2. Briefly, for each expression plate, two 96-well assay plates were prepared, one plate coated with AF10 antibody only, and the second with the immunocomplex of 25-(OH)D$_3$:AF10. The culture supernatants from the expression plate were transferred to the corresponding well of the assay plate. After 1 hour incubation at room temperature, the samples were washed three times with PBS-TWEEN®. 100 μl of HRP-conjugated anti-Fab antibody (Jackson ImmunoReaearch Lab, USA) were added to each well for 1 hour incubation at room temperature. After 3 times wash with PBS-TWEEN®, 100 μl of substrate TMB was added to each well for 10-30 min development, and 50 μl of stop solution was added. OD450 was then measured. The clones that bound to the immunocomplex of 25-(OH)D$_3$:AF10 but not AF10 antibody alone were selected for confirmation. 1:3 serial dilutions of the positive culture supernatants were assayed following above procedure. FIG. 3 shows the binding activity of five clones to the immunocomplex of 25-(OH)D$_3$:AF10, with variable region sequences listed in Table 1.

Example 4

Recombinant Antibody Expression and Purification

For recombinant Fab expression, VH and VL gens were cloned into *E. coli* expression vector pEx. For each individual clone, 20 ml overnight cultures were prepared in 2YT with 2% glucose and 100 μg/ml Carbenicillin and incubated in a 37° C. shaker incubator. The next day, 700 mL of 2YT containing 0.1% glucose and 100 m/mL Carbenicillin was inoculated in a 2 L Ultra yield flask (Thomson Instrument Company) by transferring 7 ml of the overnight culture. The cultures were grown at 35° C. with 280 rpm shaking for approximately 2-3 hours until OD600 was ~0.8. Then 350 μl of 1M IPTG was added to the culture for overnight induction at 22° C. with 280 rpm shaking. The cells pellets were collected by centrifugation at 7500×g for 20 minutes, and resuspended into lysis buffer containing 1 mg/ml lysozyme and 5 mM EDTA for 1 hour incubation at room temperature. The supernatant with soluble Fab was collected by centrifuging twice at 15,000 rpm 25000×g at 4° C. The supernatant was then loaded onto a 5 ml protein-G column (GE healthcare) for Fab binding and washed wash with 50 ml PBS. Fab protein was then eluted with 0.3M acetic acid, pH3 buffer. The eluted fractions were collected, and neutralized with 0.5 volumes of 1M Tris-HCl, pH8.5 buffer. The Fab samples were buffer-exchanged to PBS, and concentrated to a concentration of 3-5 mg/ml. The Fab samples were stored at −80° C.

For IgG expression, the heavy chain variable domains and light chain variable domains were cloned into a cytomegalovirus promoter-based mammalian expression vectors PMX30 and pMX31, respectively. The heavy chain and light chain vector DNA was mixed in a ratio of 1:3 and transiently transfected into a 30 ml suspension HEK293 cells in serum-free medium. After 20 hours, cells were sampled to determine viability and viable cell count, and titer was measured (Octet QKe, ForteBio). The cultures were harvested at day 5, and an additional sample for each was measured to determine cell density, viability, and titer. The conditioned media containing IgG was harvested and clarified from the transient transfection production by centrifugation and filtration. The supernatant was run over a Protein A column and eluted with a low pH buffer (pH=3). Filtration using a 0.2 μm membrane filter was performed before aliquoting. After purification and filtration, the protein concentration was calculated based on the OD280 and the extinction coefficient. Generally, 1-5 mg of IgG was generated from this procedure.

Example 5

Sandwich ELISA Assay for Serum 25-(OH)D Measurement

A monoclonal antibody to the immunocomplex of 25-(OH)D:AF10 were used to prepare a sandwich based ELISA assay. Free 25-(OH)D$_3$ was used for the assay. Briefly, 100 μL/well of AF10 antibody (3 μg/ml in PBS) was used to coat the microtiter plate overnight at 4° C.

Figure 4:
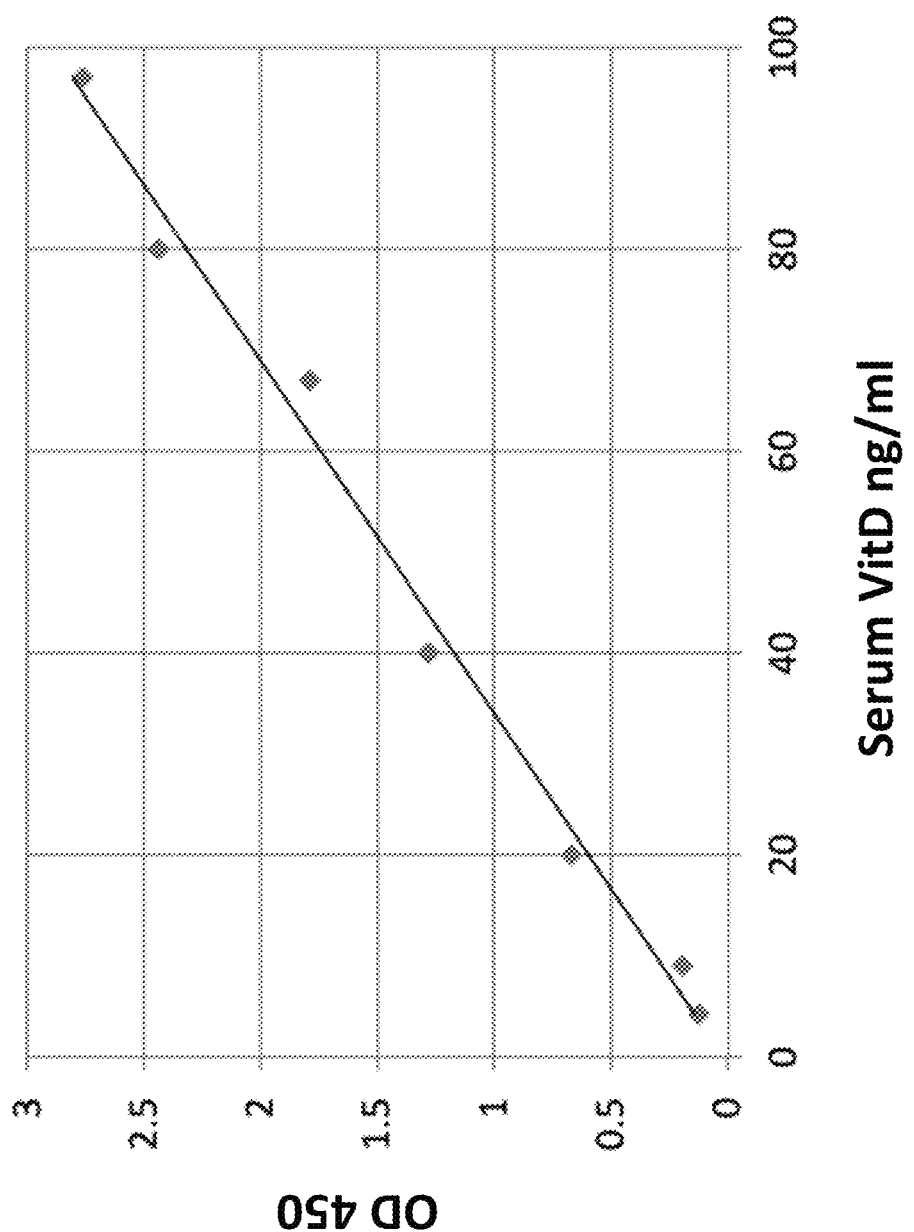
FIG. 4 illustrates a linear relationship between serum vitamin D levels and the signal of a sandwich ELISA using an antibody that specifically binds the immunocomplex of 25-(OH)D:AF10 antibody.

The assay plates were washed with PBS and blocked with 1×CHEMIBLOCKER® for 2 hours at room temperature. 5 μL/well of 25-(OH)D$_3$ at concentration of 0.5-50 ng/ml was added to the plate, and 200 μL of anti-imunocomplex antibody at 3 μg/ml was added thereafter. After 1 hour incubation at room temperature, the plate was washed 3 times with PBS-TWEEN®, and 100 μl of HRP-conjugated goat anti-mouse antibody (Jackson ImmunoReaearch Lab, USA) was added to each well for a 30-minutes incubation at room temperature. After washing three times with PBS-TWEEN®, 100 μl of substrate TMB was added to each well for a 30-minute development. 50 μL of stop solution was added, and OD450 was measured. This data showed a dose-dependent response and served as proof-of-concept for a sandwich ELISA for 25-(OH)D detection. To further confirm the utility of the assay for clinical sample detection, patient serum samples with 25-(OH)D values (as determined by ADVIA Centaur VitaminD Total assay, Siemens) were measured using the sandwich ELISA assay. The assay was performed as for the free 25-(OH)D$_3$, except that to each well 200 μL of CalBiotech release buffer (Calbiotech, California, USA) containing 3 μg/ml of the monoclonal antibody to the immunocomplex of 25-(OH)D:AF10 was added, followed by 5 μl of the serum sample. After mixing, the plate was incubated at room temperature for 1.5 hours. FIG. 4 shows a successful sandwich ELISA detection of serum 25-(OH)D, demonstrating a linear relationship between the two methods of measuring vitamin D concentration.

Example 6

Lateral Flow Assay for 25-(OH)D Measurement

An exemplary lateral flow device comprises a sample application unit (e.g., from Ahlstrom or Millipore) for sample transportation, a conjugate pad comprising labeled antibody and a detection zone comprising immobilized capture reagents and an absorbent pad (e.g., from Ahlstrom or Millipore).

Dry conjugate pad was prepared as follows. A 0.04% colloidal solution was prepared by reducing gold chloride with sodium citrate at boiling temperature. 25 μg of anti-25-(OH)D antibody was added to 1 ml of 0.04% colloidal solution and incubated at room temperature for 30 minutes. The conjugate was then centrifuged for 20 min at 10000 rpm. The supernatant was then decanted, and the pellet suspended in 1 mL of 15 mM phosphate buffer, pH 7.4. A similar procedure was performed to prepare the conjugate of colloidal gold-anti-chicken IgG antibody used for the positive control. The anti-25-(OH)D conjugate and the anti-chicken IgG conjugate were mixed with conjugate pad base in a 1:10 ratio. 10 ml of the conjugate pad base mixture was applied to a piece of 8 cm×8 cm fiberglass sheet, and vacuum dried at room temperature for 4 hours. The pad was stored with desiccant in a dry room.

To prepare the detection membrane, the monoclonal antibody to the immunocomplex of 25-(OH)D:AF10 was prepared in 15 mM phosphate buffer at pH 7.4 at the range of concentration of 0.2-1.5 mg/ml as the test line solution. The test line solution was dispensed on to nitrocellulose membrane (Millipore 125 or GE AE99) at an amount between 0.6-1.0 μL/cm. Similarly, the control line solution with anti-chicken IgG was dispensed onto the nitrocellulose membrane at the control line position. The membrane was then allowed to air-dry in an environment with less than 30% humidity for one hour, and then stored with desiccant in a dry room.

In order to construct the test device, the detection membrane, conjugate pad, and sample wicking materials were aligned and the assembled strip was placed into plastic housing.

Figure 5:
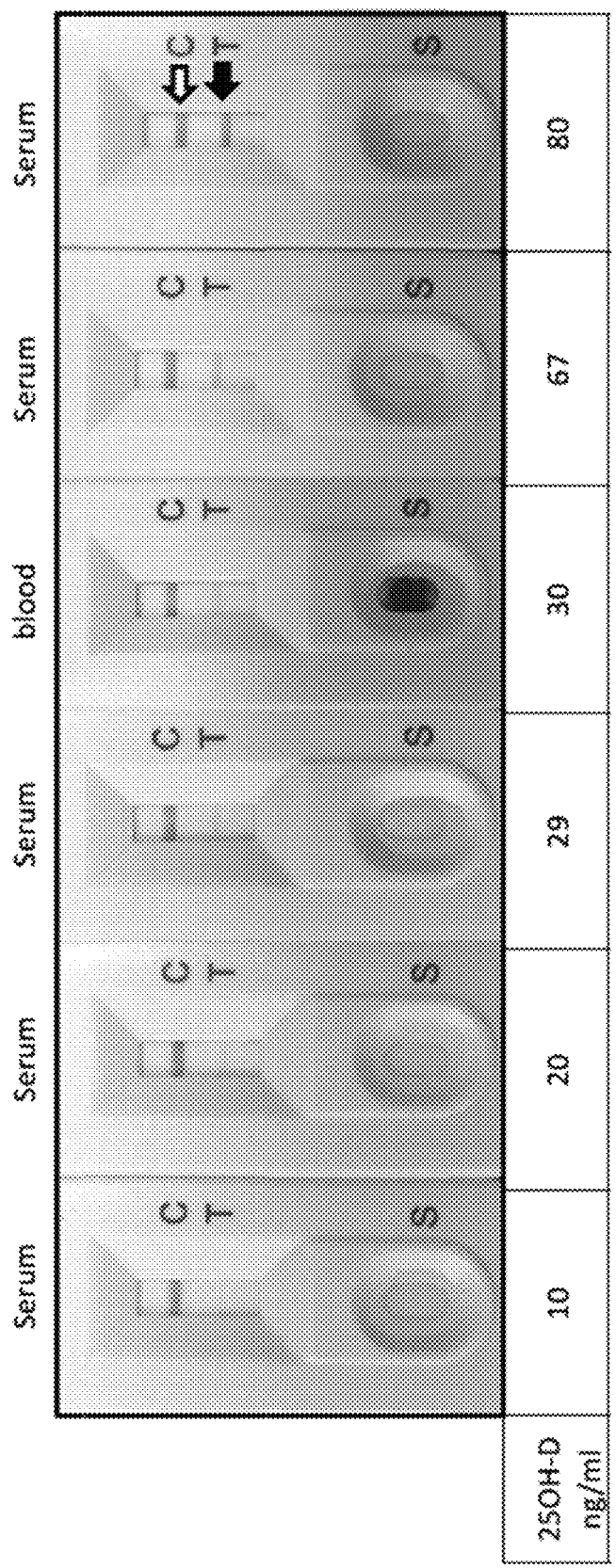
FIG. 5 displays the results of using an exemplary lateral flow device to test 25-(OH)D levels in subject blood and serum, showing a linear correlation between signal strength and 25-(OH)D levels ranging from 10 ng/ml to 80 ng/ml.

The device was evaluated by using serum or blood samples with known 25-(OH)D concentrations. 5 μL of serum or 10 μL of capillary blood was applied to the sample pad, followed by 3 drops (100 μL) of sample chase buffer. The test line and control line were read after 15 min. The results, shown in FIG. 5, indicate that the density of signal on the test line increased in samples with higher serum vitamin D concentrations. The test device indicates that a subject has sufficient, insufficient, or deficient vitamin D (FIG. 1A). Furthermore, the test device demonstrated a linear relationship between signal intensity and 25-(OH)D levels in samples ranging from 10 ng/ml to 80 ng/ml. Additional samples were tested for vitamin D levels as measured using a semi-quantitative color chart (FIG. 1B). The data were compared with the vitamin D levels determined by ADVIA Centaur VitD Assay. As shown in TABLE 4, the results of the lateral flow test device were consistent with the test from ADVIA Centaur VitD assay. The tests were reproduced with the devices from different production lot.

TABLE 4

Comparison of measurements using lateral flow test device and ADVIA Centaur VitD Assay

| Patient # | Patient ID | ADVIA Centaur VitD Assay 25-(OH)D ng/mL | Lateral flow test results (Semi-Quantitative) 25-(OH)D ng/mL | VitD Sufficiency |
|---|---|---|---|---|
| 1 | 03928913 | 4.2 | <10 | Deficient |
| 2 | 03928920 | 4.2 | <10 | Deficient |
| 3 | 1023110935 | 9 | ≤10 | Deficient |
| 4 | 1023110936 | 10 | 10 | Deficient |
| 5 | 1023110968 | 10 | 10 | Deficient |
| 6 | 1023110755 | 10 | 10 | Deficient |
| 7 | 1023110768 | 10 | ≤10 | Deficient |
| 8 | 1022110849 | 11 | 10 | Deficient |
| 9 | 1023110943 | 11 | 10 | Deficient |
| 10 | 1023110949 | 11 | 10 | Deficient |
| 11 | 1023110957 | 19.4 | ≤20 | Insufficient |
| 12 | 1023110763 | 20 | 20 | Insufficient |
| 13 | 1023110788 | 20 | ≥20 | Insufficient |
| 14 | 1023110831 | 20 | 20 | Insufficient |
| 15 | 1023110866 | 20 | ≤20 | Insufficient |
| 16 | 1023110876 | 20 | 20 | Insufficient |
| 17 | 1023110958 | 20 | 20 | Insufficient |
| 18 | 1023110743 | 21 | 20 | Insufficient |
| 19 | 1022110782 | 29 | 30 | Sufficient |
| 20 | 1022110783 | 29 | 30 | Sufficient |
| 21 | 1022110784 | 30 | ≥30 | Sufficient |
| 22 | 1022110863 | 30 | 30 | Sufficient |
| 23 | 1023110910 | 30 | 30 | Sufficient |
| 24 | 1023110813 | 29.1 | 30 | Sufficient |
| 25 | 10411110254 | 32.7 | 30 | Sufficient |
| 26 | 10411110267 | 33.5 | ≥30 | Sufficient |
| 27 | 10052015WK | 42 | >30 | Sufficient |
| 28 | 10052015JA | 41 | >30 | Sufficient |
| 29 | 1120834 | 67 | >>30 | Sufficient |
| 30 | 1124761 | 80 | >>30 | Sufficient |
| 31 | 1123647 | 97 | >>30 | Sufficient |

Figure 6:
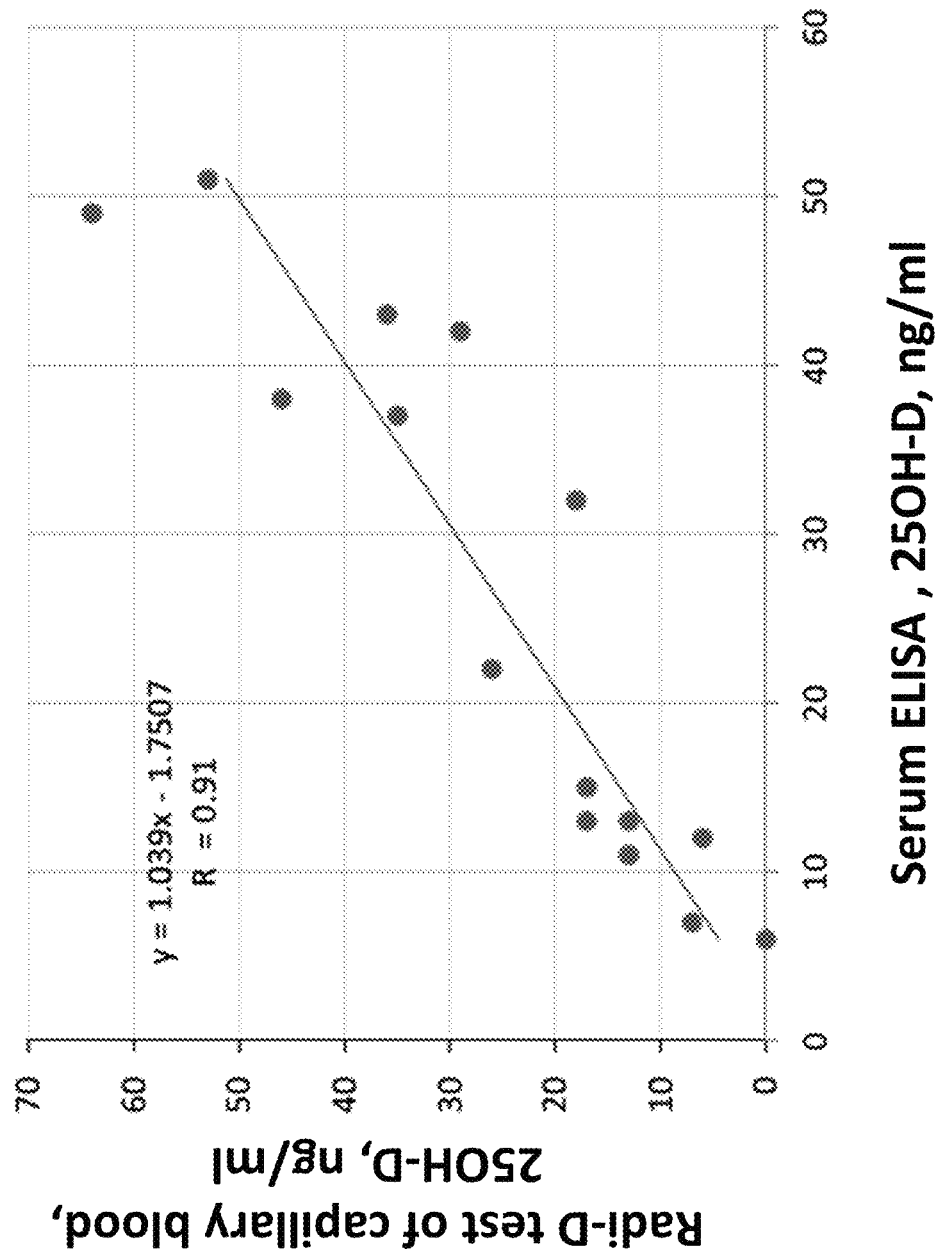
FIG. 6 illustrates the results of a comparison between vitamin D levels in as measured using (i) an exemplary lateral flow device to measure vitamin D levels of capillary blood as measured by a smartphone-based reader and (ii) an ELISA-based serum and or blood test.

Furthermore, a smartphone-based reader was used for quantitative detection of vitamin D levels in capillary blood samples. 10 μl of capillary blood was applied to the sample pad, followed by 3 drops (100 μl) of sample chase buffer. The test lines were read after 15 minutes. The serum samples of corresponding individuals were collected and subjected to an ELISA test. FIG. 6 shows the comparison between the capillary blood test using the lateral flow test device and an ELISA-based serum test. The data shows a positive linear correlation with a correlation coefficient, R, of 0.91.

Example 7

Lateral Flow Assay for 25-(OH)D Measurement Using Cube-Reader

Figure 8:
FIG. 8 shows an exemplary vitamin D measurement procedure using a portable lateral flow assay reader.
Figure 8:
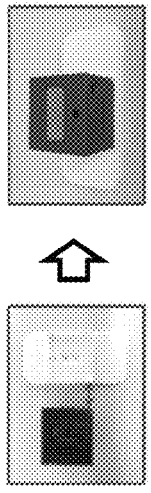
Figure 8:
Figure 8:
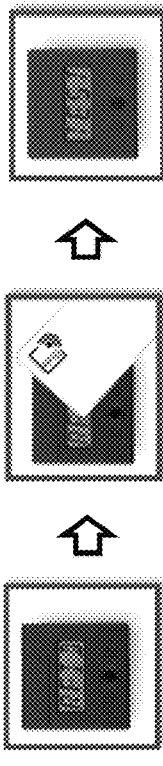
Figure 8:
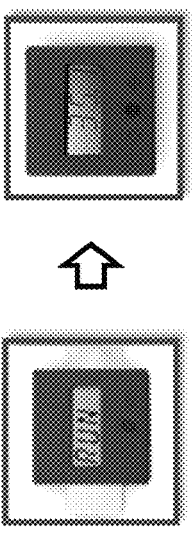

The Cube-Reader (from opTricon GmbH, Germany) was used for fully quantitative measurement of 25-OH vitamin D. Cube-Reader is a portable lateral flow assay reader, with a cube-shape at an edge length of approximate 41 mm and weigh of 40 g. The measurement procedure is shown in FIG. 8.

Total 20 human serum samples with 25-OH Vitamin D values determined by Liquid Chromatography Mass Spectrometry (LC-MS/MS) assay were applied to lateral flow test. The measurement procedure is described in the Example 6. The results listed in Table 5 show that the 25-OH vitamin D values from lateral flow test are very close to the true values generated from LC-MS/MS assay (a "gold" standard method for 25-OH vitamin D measurement).

TABLE 5

Test Results from Lateral Flow Test and Liquid Chromatography Mass Spectrometry Test

| Sample ID | 25-OH Vitamin D (ng/ml) LC-MS/MS test | 25-OH Vitamin D (ng/ml) Lateral flow test |
|---|---|---|
| S-1 | 14.3 | 14.4 |
| S-2 | 14.0 | 16.0 |
| S-3 | 18.9 | 19.9 |
| S-4 | 19.8 | 19.1 |
| S-5 | 20.0 | 22.4 |
| S-6 | 26.4 | 22.1 |
| S-7 | 29.3 | 31.0 |
| S-8 | 40.1 | 37.2 |
| S-9 | 40.3 | 47.4 |
| S-10 | 45.9 | 51.8 |
| S-11 | 46.4 | 39.2 |
| S-12 | 49.0 | 42.6 |
| S-13 | 56.3 | 57.4 |
| S-14 | 60.3 | 72.7 |
| S-15 | 63.1 | 67.8 |
| S-16 | 75.5 | 71.2 |
| S-17 | 87.4 | 85.9 |
| S-18 | 92.3 | 97.9 |
| S-19 | 92.4 | 94.4 |
| S-20 | 103.9 | 93.1 |
| Average | 49.8 | 50.2 |

Figure 9:
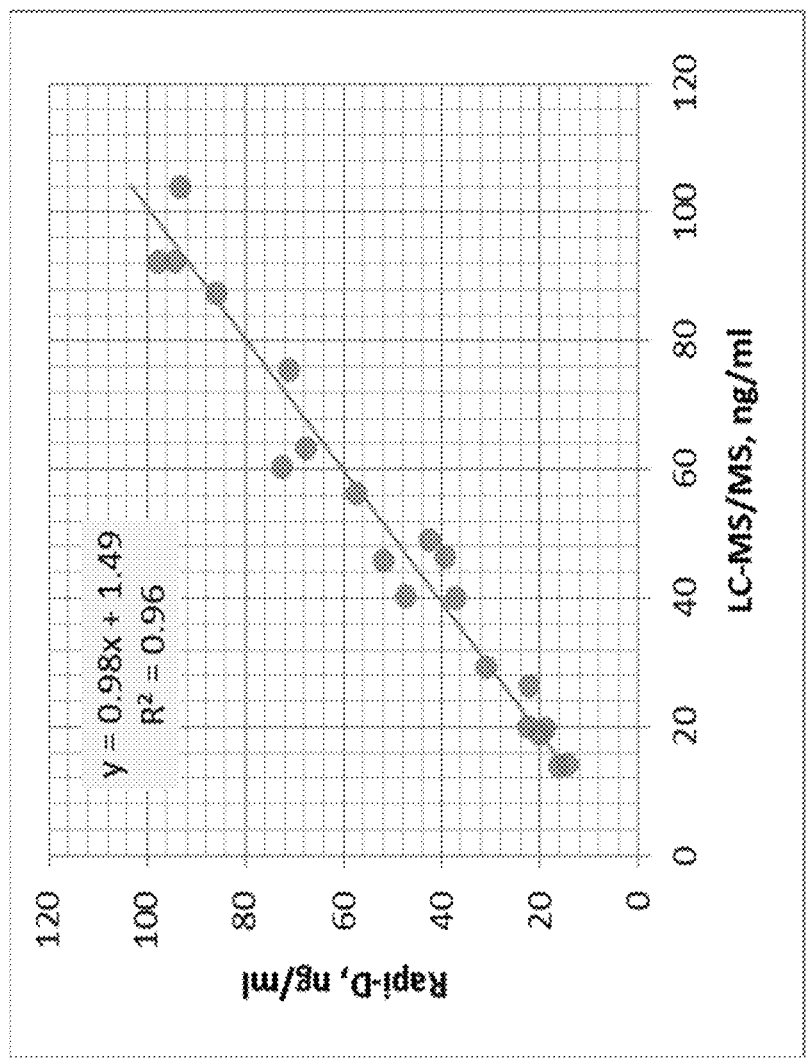
FIG. 9 shows a correlation between test results generated from a lateral flow assay and a liquid chromatography-tandem mass spectrometry assay.

The comparison of 25-OH vitamin D values between lateral flow test and LC-MS/MS assay yield a linear regression Y=0.98x+1.49, with correlation coefficient of 0.98. The comparison result is illustrated in the FIG. 9.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A test device for detecting one or more vitamin D molecules comprising:
  a housing, containing therein:
    (a) a sample application pad configured to absorb a biological sample and transport said biological sample to a conjugate pad;
    (b) said conjugate pad, wherein said conjugate pad comprises a vitamin D binding agent that specifically binds to one or more vitamin D molecules; and
    (c) a detection zone comprising a first region having immobilized thereon a detection agent that specifically binds an epitope that is generated by complexing said vitamin D binding agent with said one or more vitamin D molecules,
  wherein said detection agent is an antibody comprising a light chain and a heavy chain, wherein said light chain comprises an amino acid sequence selected from the group consisting of SEQ ID NOs: 1, 2, 3, 4, 5, 16, 17, 18, 19, and 20; and wherein said heavy chain comprises an amino acid sequence selected from the group consisting of SEQ ID NOs: 6, 7, 8, 9, 10, 11, 12, 13, 14, and 15.

2. The test device of claim 1, wherein said one or more vitamin D molecules are selected from the group consisting of 25-hydroxyvitamin $D_2$, 25-hydroxyvitamin $D_3$, 25-hydroxyvitamin $D_4$, 25-hydroxyvitamin $D_5$, and 1,25-hydroxyvitamin $D_3$.

3. The test device of claim 1, wherein said one or more vitamin D molecules are selected from the group consisting of 25-hydroxyvitamin $D_2$ and 25-hydroxyvitamin $D_3$.

4. The test device of claim 1, wherein said one or more vitamin D molecules are 25-hydroxyvitamin $D_2$ and 25-hydroxyvitamin $D_3$.

5. The test device of claim 1, wherein said one or more vitamin D molecules consist of 25-hydroxyvitamin $D_2$.

6. The test device of claim 1, wherein said one or more vitamin D molecules consist of 25-hydroxyvitamin $D_3$.

7. The test device of claim 1, wherein said detection zone further comprises a second region having immobilized thereon an antibody that is capable of binding to said vitamin D binding agent whether or not said vitamin D binding agent is bound to said one or more vitamin D molecules.

8. The test device of claim 1, wherein said vitamin D binding agent is conjugated to a detection reagent.

9. The test device of claim 1, wherein said sample application pad, said conjugate pad, and said detection zone are aligned from upstream to downstream along a fluid path through which said biological sample travels.

10. The test device of claim 1, further comprising a filtering component between said sample application pad and said conjugate pad configured to separate a particulate portion of said biological sample from an aqueous portion of said biological sample.

11. The test device of claim 1, wherein said detection agent is an antibody comprising a light chain and a heavy chain, wherein:
  (i) said light chain comprises the amino acid sequence of SEQ ID NO: 20, and said heavy chain comprises the amino acid sequence of SEQ ID NO: 12; or
  (ii) said light chain comprises the amino add sequence of SEQ ID NO: 2, and said heavy chain comprises the amino acid sequence of SEQ ID NO: 13; or
  (iii) said light chain comprises the amino add sequence of SEQ ID NO: 19, and said heavy chain comprises the amino acid sequence of SEQ ID NO: 9.

12. A method for detecting one or more vitamin D molecules in a biological sample, comprising:
  (a) applying said a biological sample to said sample application pad of said test device of claim 1;
  (b) applying a chase buffer to said sample application pad; and
  (c) detecting said one or more vitamin D molecules using said test device of claim 1.

13. The method of claim 12, further comprising quantifying said one or more vitamin D molecules in said biological sample.

14. The method of claim 13, wherein said quantifying classifies said biological sample as having a sufficient level, an insufficient level, or a deficient level of said one or more vitamin D molecules.

15. The method of claim 13, wherein said quantifying comprises quantifying a concentration of about 3 ng/ml to about 105 ng/ml of said one or more vitamin D molecules in said biological sample.

16. The method of claim 14, wherein said sufficient level is at least 30 ng/mL.

17. The method of claim 14, wherein said insufficient level is at least 10 ng/mL and less than 30 ng/mL.

18. The method of claim 14, wherein said deficient level is less than 10 ng/mL.

19. The method of claim 13, wherein said quantifying comprises using: (i) an imaging device to provide an image of said detection zone; and (ii) software on a programmed computer configured to quantify said one or more vitamin D molecules in said biological sample based on said image of said detection zone.

20. The method of claim 12, wherein said chase buffer comprises reagents to dissociate said one or more vitamin D molecules from vitamin D binding protein.

21. The method of claim 12, wherein said biological sample is selected from the group consisting of whole blood, serum, plasma, urine, saliva, ocular fluid, spinal fluid, and perspiration.

22. A method for detecting one or more vitamin D levels in a biological sample with a test device configured to perform a binding assay, comprising:
  (a) contacting said biological sample with the test device of claim 1;
  (b) subjecting said biological sample to said binding assay, wherein said binding assay comprises forming a complex between (i) said vitamin D binding agent in said conjugate pad; and (ii) one or more vitamin D molecules in said biological sample;

(c) further exposing said complex to said detection agent immobilized in the detection zone, and detecting said one or more vitamin D molecules by detecting binding of said complex to said detection agent.

23. A kit, comprising:
(a) said test device of claim 1; and
(b) written instructions for use of said kit.

* * * * *

SEQUENCE LISTING

<160> NUMBER OF SEQ ID NOS: 21

<210> SEQ ID NO 1
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Asp Ile Gln Met Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Ser Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

Asp Ile Val Leu Thr Gln Ser Gln Lys Phe Met Ser Thr Ser Val Gly

```
1               5                   10                  15
Asp Arg Val Ser Val Thr Cys Lys Ala Ser Gln Asn Val Gly Thr Asn
                20                  25                  30
Val Ala Trp Tyr Gln Gln Lys Pro Gly Gln Ser Pro Lys Ala Leu Ile
            35                  40                  45
Tyr Ser Ala Ser Tyr Arg Tyr Ser Gly Val Pro Asp Arg Phe Thr Gly
        50                  55                  60
Ser Gly Ser Gly Thr Asp Phe Thr Leu Thr Ile Ser Asn Val Gln Ser
65                  70                  75                  80
Glu Asp Leu Ala Glu Tyr Phe Cys Gln Gln His Tyr Ser Thr Pro Tyr
                85                  90                  95
Thr Phe Gly Gly Gly Thr Lys Leu Glu Ile Lys
            100                 105
```

<210> SEQ ID NO 3
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Lys Ser Val Ser Thr Ser
                20                  25                  30
Gly Tyr Ser Tyr Met His Trp Tyr Gln Gln Lys Pro Gly Gln Pro Pro
            35                  40                  45
Lys Leu Leu Ile Tyr Leu Ala Ser Asn Leu Glu Ser Gly Val Pro Ala
        50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln Gln Ser Asn
                85                  90                  95
Glu Asp Pro Phe Thr Phe Gly Ser Gly Thr Lys Leu Glu Leu Lys
            100                 105                 110
```

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Asp Ile Val Leu Thr Gln Ser Pro Ser Ser Leu Ser Ala Ser Leu Gly
1               5                   10                  15
Glu Arg Val Ser Leu Thr Cys Arg Ala Ser Gln Asp Ile Gly Ser Ser
                20                  25                  30
Leu Asn Trp Leu Gln Gln Glu Pro Asp Gly Thr Ile Lys Arg Leu Ile
            35                  40                  45
Tyr Ala Thr Ser Ser Leu Asp Ser Gly Val Pro Lys Arg Phe Ser Gly
        50                  55                  60
Ser Arg Ser Gly Ser Asp Tyr Ser Leu Thr Ile Ser Ser Leu Glu Ser
65                  70                  75                  80
Glu Asp Phe Val Asp Tyr Tyr Cys Gln Gln His Gly Glu Ser Pro Leu
```

```
                85                  90                  95
Thr Phe Gly Ala Gly Thr Lys Leu Glu Ile Lys
                100                 105

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ala Ser Ser Pro Tyr
                85                  90                  95

Thr Phe Gly Gly Gly Thr Lys Leu Glu Ile Lys
                100                 105

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Val Val Tyr Tyr Cys
                85                  90                  95

Ala Arg Gln Asp Gly Tyr Tyr Val Gly Tyr Phe Asp Tyr Trp Gly Gln
                100                 105                 110

Gly Thr Thr Leu Thr Val Ser Ser
        115                 120

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 7

```
Glu Val Glu Leu Gln Glu Ser Gly Ala Glu Leu Val Arg Pro Gly Ala
1               5                   10                  15

Ser Val Lys Leu Ser Cys Lys Ala Ser Gly Tyr Ser Phe Thr Asn Tyr
            20                  25                  30

Trp Met Asn Trp Val Arg Gln Arg Pro Gly Gln Gly Phe Glu Trp Ile
        35                  40                  45

Gly Glu Ile Asn Pro Ser Asn Gly Asp Thr Phe Tyr Asn Gln Lys Phe
    50                  55                  60

Lys Gly Lys Ala Thr Leu Ile Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ile Gly Gly Tyr Tyr Phe Asp Tyr Trp Gly Gln Gly Thr Thr
            100                 105                 110

Leu Thr Val Ser Ser
        115
```

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Glu Val Asn Val Val Glu Ser Gly Ala Glu Leu Val Lys Pro Gly Ala
1               5                   10                  15

Ser Val Arg Leu Ser Cys Thr Thr Ser Gly Phe Asn Ile Glu Asp Ser
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Ile Lys Ser Asp Pro Lys Phe
    50                  55                  60

Gln Gly Lys Ala Thr Ile Ser Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Leu Tyr Tyr Tyr Asp Ser Ser Asp Tyr Trp Gly Gln Gly Thr Thr Leu
            100                 105                 110

Thr Val Ser Ser
        115
```

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Glu Val Lys Leu Val Glu Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30
```

-continued

Asn Met Asn Trp Val Lys Gln Ser Asn Gly Lys Ser Leu Glu Trp Ile
            35                  40                  45

Gly Asn Ile Asp Pro Tyr Tyr Gly Gly Thr Ser Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Trp Ser Tyr Tyr Gly Asn Tyr Val Tyr Trp Tyr Phe Asp Val
            100                 105                 110

Trp Gly Ala Gly Thr Thr Leu Thr Val Ser Ser
            115                 120

<210> SEQ ID NO 10
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Ser Tyr Tyr Phe Asp Tyr Trp Gly Gln Gly Thr Thr Leu Thr
            100                 105                 110

Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Val Asn Trp Val Arg Gln Ala Pro Gly Lys Gly Leu Glu Trp Leu
        35                  40                  45

Ser Val Ile Ser Gly Asp Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Ala Leu Asn Ala Gly Trp Gly Phe Asp Tyr Trp Gly Gln Gly
            100                 105                 110

Thr Leu Val Thr Val Ser Ser
        115

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Gly Ser
            20                  25                  30

Ala Met His Trp Val Arg Gln Ala Pro Gly Lys Gly Met Glu Trp Val
        35                  40                  45

Ser Ala Ile Ser Gly Ser Gly Gly Ser Thr Tyr Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Gly Tyr Thr Asp Gly Tyr Gly Met Asp Tyr Trp Gly Gln
            100                 105                 110

Gly Thr Leu Val Thr Val Ser Ser
        115                 120

<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Ser Val Asn Trp Val Arg Gln Ala Pro Gly Lys Gly Leu Glu Trp Leu
        35                  40                  45

Ala Val Ile Ser Gly Asp Gly Gly Ser Thr Tyr Tyr Ala Asp Ser Val
    50                  55                  60

Lys Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ile Phe Pro Ser Tyr Met Asp Val Trp Gly Gln Gly Thr
            100                 105                 110

Leu Val Thr Val Ser Ser
        115
```

```
<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Asp Trp Val Arg Gln Ala Arg Gly Gln Arg Leu Glu Trp Ile
        35                  40                  45

Gly Trp Ile Val Val Gly Ser Gly Asn Thr Ser Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Ser Val Thr Tyr Tyr Tyr Met Asp His Trp Gly Gln Gly Thr
            100                 105                 110

Leu Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser Tyr
            20                  25                  30

Ala Ile Ser Trp Val Arg Gln Ala Pro Gly Gln Gly Leu Glu Trp Met
        35                  40                  45

Gly Val Ile Ile Gly Ile Phe Gly Thr Ala Thr Tyr Ala Gln Ser Val
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Arg Tyr Ser Arg Ser Phe Asp Val Trp Gly Gln Gly
            100                 105                 110

Thr Leu Val Thr Val Ser Ser
        115

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Asn Arg Leu Val Ser Ser Ser
            20                  25                  30

Met Leu Ala Trp Tyr Gln Gln Lys Pro Gly Gln Ala Pro Arg Leu Leu
        35                  40                  45

Ile Gly Ala Ser Lys Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Ala Gln Tyr Asp Gly Ser Ser Tyr
                85                  90                  95

Thr Phe Gly Gln Gly Thr Lys Leu Glu Ile Lys Arg
            100                 105

<210> SEQ ID NO 17
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ser Val Leu Thr Gln Pro Pro Ser Val Ser Gly Ser Pro Gly Gln
1               5                   10                  15

Arg Val Thr Ile Ser Cys Thr Gly Asn Asn Leu Ser Gly Tyr Tyr Val
            20                  25                  30

Ser Trp Tyr Gln Gln Leu Pro Gly Thr Ala Pro Lys Leu Leu Ile Tyr
        35                  40                  45

Gly Asn Ser Asn Arg Pro Ser Gly Val Pro Asp Arg Phe Ser Gly Ser
    50                  55                  60

Lys Ser Gly Thr Ser Ala Ser Leu Ala Ile Thr Gly Leu Gln Ala Met
65                  70                  75                  80

Asp Glu Ala Asp Tyr Tyr Cys Ala Ala Tyr Tyr Ser Gly Thr Tyr Val
                85                  90                  95

Phe Gly Gln Gly Thr Lys Leu Thr Val Leu Gly Gln
            100                 105

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Tyr Glu Leu Thr Gln Pro Leu Ser Val Ser Val Ser Leu Gly Gln
1               5                   10                  15

Thr Ala Arg Ile Thr Cys Trp Asp Asn Val Gly Gly Tyr Asn Val His
            20                  25                  30

Trp Tyr Gln Gln Lys Pro Gly Gln Ser Pro Val Leu Val Ile Tyr Arg
        35                  40                  45

Asp Ser Glu Arg Pro Ser Gly Ile Pro Glu Arg Phe Ser Gly Ser Asn
    50                  55                  60

Ser Gly Asn Thr Ala Thr Leu Thr Ile Ser Arg Ala Gln Ala Gly Asp
65                  70                  75                  80

Glu Ala Asp Tyr Tyr Cys Ser Ser Tyr Tyr Gln Ser Thr Val Leu Phe
                85                  90                  95

Gly Gly Gly Thr Lys Leu Thr Val Leu Gly Gln
            100                 105

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Asn Val Gly Gly Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ser Ala Tyr His Gln Ser Thr Tyr
                85                  90                  95

Thr Phe Gly Gln Gly Thr Lys Val Glu Ile Lys Arg
            100                 105

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Val Gly Ser Ser Tyr
            20                  25                  30

Val Asn Trp Tyr Gln Gln Lys Pro Gly Lys Ala Pro Lys Leu Leu Ile
        35                  40                  45

Tyr Ala Ala Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ser Tyr Tyr Ser Thr Ser Thr
                85                  90                  95

Phe Gly Gly Gly Thr Lys Val Glu Ile Lys Arg
            100                 105

<210> SEQ ID NO 21
<211> LENGTH: 16
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 21

Gly Ser Ser Ser Gly Ser Ser Ser Gly Ser Ser Ser Gly Ser Ser Ser
1               5                   10                  15
```